(12) United States Patent
Acharya et al.

(10) Patent No.: US 11,207,343 B2
(45) Date of Patent: Dec. 28, 2021

(54) COMPOSITIONS AND THERAPEUTIC METHODS

(71) Applicant: AyuVis Research LLC, Fort Worth, TX (US)

(72) Inventors: Suchismita Acharya, Euless, TX (US); Santosh K Panda, Gaithersburg, MD (US); Pragnya Das, Secane, PA (US); Beamon Agarwal, Secane, PA (US)

(73) Assignee: AYUVIS RESEARCH, INC., Fort Worth, TX (US)

( * ) Notice: Subject to any disclaimer, the term of this patent is extended or adjusted under 35 U.S.C. 154(b) by 0 days.

(21) Appl. No.: 15/473,904

(22) Filed: Mar. 30, 2017

(65) Prior Publication Data

US 2017/0281667 A1    Oct. 5, 2017

Related U.S. Application Data

(60) Provisional application No. 62/315,144, filed on Mar. 30, 2016.

(51) Int. Cl.

| A61K 31/715 | (2006.01) |
| A61K 9/10 | (2006.01) |
| A61K 45/06 | (2006.01) |
| A61K 9/00 | (2006.01) |
| A61K 47/32 | (2006.01) |
| A61K 47/10 | (2017.01) |
| A61K 47/44 | (2017.01) |
| A61K 47/02 | (2006.01) |
| A61K 9/06 | (2006.01) |

(52) U.S. Cl.
CPC .............. *A61K 31/715* (2013.01); *A61K 9/10* (2013.01); *A61K 45/06* (2013.01); *A61K 9/0014* (2013.01); *A61K 9/0019* (2013.01); *A61K 9/0048* (2013.01); *A61K 9/06* (2013.01); *A61K 47/02* (2013.01); *A61K 47/10* (2013.01); *A61K 47/32* (2013.01); *A61K 47/44* (2013.01)

(58) Field of Classification Search
CPC ......... A61K 31/715; A61K 9/10; A61K 45/06
See application file for complete search history.

(56) References Cited

U.S. PATENT DOCUMENTS

| 4,152,413 | A | 5/1979 | Goodnow |
| 6,441,088 | B1 | 8/2002 | Kaul et al. |
| 2002/0022601 | A1 | 2/2002 | Konno et al. |
| 2003/0148997 | A1 | 8/2003 | Sackstein et al. |
| 2004/0147730 | A1* | 7/2004 | Nilsson .................. C07H 5/06 536/18.7 |
| 2005/0070500 | A1 | 3/2005 | Boucher l et al. |
| 2011/0044901 | A1 | 2/2011 | Seed et al. |
| 2013/0281395 | A1 | 10/2013 | Wipf et al. |
| 2015/0225488 | A1 | 8/2015 | Schoenfisch et al. |

FOREIGN PATENT DOCUMENTS

| CN | 101732338 | A | 6/2010 |
| CN | 102475714 | A | 5/2012 |
| EP | 183556 | A2 | 6/1986 |
| EP | 570682 | A1 | 11/1993 |
| JP | 04001115 | A | 1/1992 |
| JP | 2007099668 | A | 4/2007 |
| JP | 2007246426 | * | 9/2007 ........... C07H 15/203 |
| JP | 2007246426 | A | 9/2007 |
| WO | 2007048974 | A2 | 5/2007 |
| WO | 2014186358 | A2 | 11/2014 |

OTHER PUBLICATIONS

Berkin (Glycoconjugate Journal; 22, 443-451, 2005).*
Pharmaceutical solutions for oral administration (Chapter 1; Jul. 5, 2008, pp. 1-24).*
JP 2007246426; machine translation, translated on Jun. 17, 2019.*
Kuyama (Carbohydrate research; 143, C1-C7, 1993).*
Claudia (Carbohydrate Research; 490, 2020, 107952, pp. 1-5).*
Cho, Youngeun et al., "Toll-like Receptor Polymorphisms and Age-Related Macular Degeneration: Replication in Three Case-Control Samples" Invest Ophthalmol Vis Sci. Dec. 2009 ; 50(12): 5614-5618.
Elner, Susan et al., "TLR4 Mediates Human Retinal Pigment Epithelial Endotoxin Binding and Cytokine Expression" Investigative Ophthalmology & Visual Science, Dec. 2005, vol. 46, No. 12, 4627-4633.
He, Chang et al. "Angiogenesis Mediated by Toll-Like Receptor 4 in Ischemic Neural Tissue" Arterioscler Thromb Vasc Biol. 2013;33:330-338.
Higgins, Gareth T. et al., "Induction of Angiogenic Cytokine Expression in Cultured RPE by Ingestion of Oxidized Photoreceptor Outer Segments" Invest Ophthalmol Vis Sci. 2003;44:1775-1782.
Huang, Jiahn-Dar et al., "7-Ketocholesterol-Induced Inflammation Signals Mostly through the TLR4 Receptor Both In Vitro and In Vivo" PLoS ONE Jul. 18, 2014 9(7): 26 pages.
Kaarniranta, K. et al., "Age-related macular degeneration: activation of innate immunity system via pattern recognition receptors" J Mol Med (2009) 87:117-123.
Leon, Carlos G. et al., "Discovery and Development of Toll-Like Receptor 4 (TLR4) Antagonists: A New Paradigm for Treating Sepsis and Other Diseases" Pharmaceutical Research, vol. 25, No. 8, Aug. 2008, 1751-1761.
Mosser, David M. "The many faces of macrophage activation" Journal of Leukocyte Biology, Feb. 2003, vol. 73, No. 2 , pp. 209-212.

(Continued)

*Primary Examiner* — Pancham Bakshi
(74) *Attorney, Agent, or Firm* — Edwin S. Flores; Daniel J. Chalker; Chalker Flores, LLP

(57) ABSTRACT

The present invention is directed to novel products, variants, pharmaceutically acceptable salts and prodrugs thereof, and medical use of such compounds for the treatment and/or management of sepsis, septicemia, septic shock, ocular infection, ocular inflammation, ocular angiogenesis, rheumatoid arthritis (RA), atherosclerosis, inflammatory bowel diseases (IBD), asthma, chronic obstructive pulmonary disease, fever syndromes, cachexia, psoriasis, autoimmune diseases, cardiac diseases, retinoblastoma, cancer and/or any disorder associated with inflammation, immunomodulation and microbial infection.

10 Claims, 14 Drawing Sheets

(56) References Cited

OTHER PUBLICATIONS

Opal, Steven M. et al. "Effect of Eritoran, an Antagonist of MD2-TLR4, on Mortality in Patients With Severe Sepsis The ACCESS Randomized Trial" JAMA, Mar. 20, 2013—vol. 309, No. 11, 1154-1162.

Panda, Santosh K. et al. "Chitohexaose Activates Macrophages by Alternate Pathway through TLR4 and Blocks Endotoxemia" PLoS Pathog, May 24, 2012, 8(5), 17 pages.

Paul, Brajeswar et al. "S-, N- and O-Glycosyl Derivatives of 2-Acetamido-2-Deoxy-D-Glucose With Hydrophobic Glycons as Potential Chemotherapeutic Agents and N-Acetyl-B-D-Glucos-Aminidase Inhibitors" Carbohydrate Research, 126 (1984) 27-43.

Savva, Athina et al. "TargetingToll-like receptors: promising therapeutic strategies for the management of sepsis-associated pathology and infectious diseases" Frontiers in Immunology | Microbial Immunology, Nov. 2013 | vol. 4 | Article 387, 16 pages.

Wang, Jianyun et al. "Research of the degradation products of chitosan's angiogenic function" Applied Surface Science 255 (2008) 260-262.

Wong, Wan Ling et al. "Global prevalence of age-related macular degeneration and disease burden projection for 2020 and 2040: a systematic review and meta-analysis" The Lancet, vol. 2 Feb. 2014, e106-e116.

Xia, Wenshui et al., "Biological activities of chitosan and chitooligosaccharides" Food Hydrocolloids 25 (2011) 170-179.

Xiong, Chuannan et al. "Potent angiogenic inhibition effects of deacetylated chitohexaose separated from chitooligosaccharides and its mechanism of action in vitro" Carbohydrate Research 344 (2009) 1975-1983.

Yi, Hyun et al. "Novel Role for the Innate Immune Receptor Toll-Like Receptor 4 (TLR4) in the Regulation of the Wnt Signaling Pathway and Photoreceptor Apoptosis" May 17, 2012, PLoS ONE 7(5), 15 pages.

International Search Report and Written Opinion (PCT/US17/24908) [ISA/US] dated Aug. 17, 2017.

Cinget, Francis et al. "X-Ray structure of the 2,2,6,6-tetramethylpiperidin-1-oxyl-4-yl) 2,3,4,6-tetra-O-acetyl-B-D-glucopyranoside" Carbohydrate Research 218 (1991) 1-8.

Fukui, Koichi et al. "Soultion-state dynamics of sugar-connected spin probes in sucrose solution as studied by multiband (I-, X-, and W-band) electron paramagnetic resonance" Journal of Magnetic Resonance 163 (2003) 174-181.

Goldstein, Irwin J. et al. "Probing the Topography of Lectins with Site-Specific Spin-Labeled Glycosides" Biochemistry 1985, 24, 823-826.

Johnson, Philip E. et al. "The Cellulose-binding Domains from Cellulomonas fimi B-1,4-Glucanase CenC Bind Nitroxide Spin-labeled Cellooligosaccharides in Multiple Orientations" J. Mol. Biol. (1999) 287, 609-625.

Plessas, Nike R. et al. "Synthesis of a- and B-Glycosides Containing Spin Labels, as Probes for Studies of Carbohydrate-Protein Interaction" Carbohydrate Research, 89 (1981) 211-220.

Sato, Shingo et al. "Novel glycosylation of the nitrooxyl radicals with peracetylated glycosyl fluorides using a combination of BF3. OEt2 and an amine base as promoters" Carbohydrate Research 334 (2001) 215-222.

Sato, Shingo et al. "Synthesis and enzyme-catalyzed hydrolysis of a radical-masked glycosylated spin-label reagent" Carbohydrate Research 339 (2004) 2425-2432.

Sosnovsky, George et al. "One-step spon-labeling of unprotected d-glucose and 2-deoxy-D-arabino-hexose" Carbohydrate Research, 190 (1989) c1-c2.

Struve, William G. et al. "A New Spin-Labeled Substrate for B-Galactosidase and B-Galactoside Permease" Biochemical and Biophysical Research Communications, vol. 49, No. 6, 1972, 1631-1637.

Troganis, Anastassios et al. "Modes of association of concanavalin A with a-D-glycosides" Biochimica et Biophysica Acta 1206 (1994) 215-224.

Shoichiro Ozaki: "Sulfo Disaccharides Co-Working With Klotho Studies on Structure, Structure Activity Relation and Function", Ozaki World Journal of Pharmacy and Pharmaceutical Sciences, Jan. 1, 2015 (Jan. 1, 2015).

Toshihiko Sawada et al: "Synthesis of sulfated phenyl 2-acetamido-2-deoxy-D-galactopyranosi des. 4-0-Sulfated phenyl 2-acetamido-2-deoxy-[beta]-D-galactopyrano side is a competitive acceptor that decreases sulfation of chondroitin sulfate by N-acetylgalactosamine 4-sulfate 6-0-sulfotransferase", Carbohydrate Research, vol. 340, No. 12, Jul. 15, 2005 (Jul. 15, 2005), pp. 1983-1996.

Goran Ekborg et al: "Note p-(Tri fluoroacetami do)phenyl nosyl-/3-D-glucopyranoside* 2-acetamido-2-deoxy-4-0-fi-D-mannopyra", Carbohydrate Research Nationul Institutesof Health, Jan. 1, 1984 (Jan. 1, 1984), pp. 287-292.

Jens Landström et al.: "Combining weak affinity chromatography, NMR spectroscopy and molecular simulations in carbohydrate-lysozyme interaction studies" Organic & Biomolecular Chemistry, vol. 10, No. 15, Jan. 1, 2012 (Jan. 1, 2012).

Vania Olivon: "Acute increases of O-GlcNAcylation reduces sepsis-associated mortality (837.8) | The FASEB Journal", Apr. 1, 2014 (Apr. 1, 2014).

Santosh K. Panda et al: "Chitohexaose Activates Macrophages by Alternate Pathway through TLR4 and Blocks Endotoxemia", PLOS Pathogens, vol. 8, No. 5, May 24, 2012 (May 24, 2012), page e1002717.

EESR EP 17776618.5 dated Nov. 19, 2019.

* cited by examiner

* P < 0.05 compared to only cell lysate (Unpaired t test)

| Compound | E. Coli | P. Aeruginosa | K. Pneumoniae | A. Baumannii | S. Aureus | C. albicans |
|---|---|---|---|---|---|---|
| | MIC$_{90}$ mg/L | MIC$_{90}$ mg/L | MIC$_{90}$ mg/L | MIC$_{90}$ mg/L | MIC$_{90}$ mg/L | MIC$_{90}$ mg/L |
| Colistin | 1 | 4 | 128 | 4 | >128 | NA |
| Fluconazole | NA | NA | NA | NA | NA | >128 |
| 13 | 200 | 200 | 200 | 200 | >200 | 200 |
| 14 | 200 | 200 | 200 | 200 | >200 | 200 |

Fig. 13 (Continued)

| 12 | 50 | 200 | 100 | 100 | 200 | 200 |
|---|---|---|---|---|---|---|
| 15 | 50 | 100 | 50 | 50 | 200 | 100 |
| 27 | 100 | 100 | 200 | 200 | 200 | 200 |
| 4 | 200 | 200 | 200 | 200 | 200 | 100 |
| 1 | 200 | 100 | 100 | 100 | 100 | 50 |
| 2 | Resistant | >200 | Resistant | Resistant | Resistant | Resistant |

Fig. 14

| Compound | $MIC_{90}$ | | $MBEC_{90}$ | | $MBIC_{90}$ | |
|---|---|---|---|---|---|---|
| | MRSA | MSSA | MRSA | MSSA | MRSA | MSSA |
| Colistin | >128 | 128 | 128 | 32 | >128 | 100 |
| 1 | 100 | 100 | 200 | 200 | 200 | 100 |
| 12 | 100 | 100 | 200 | 200 | 200 | 100 |
| 15 | 200 | 50 | 200 | 100 | 100 | 50 |

COMPOSITIONS AND THERAPEUTIC METHODS

CROSS-REFERENCE

This application claims the benefit of U.S. Provisional Application No. 62/315,144 filed Mar. 30, 2016, which application is incorporated herein by reference.

TECHNICAL FIELD OF THE INVENTION

The present invention is directed to novel products, variants, pharmaceutically acceptable salts and prodrugs thereof, and medical use of such compounds for the treatment and/or management of sepsis, septicemia, septic shock, ocular infection, ocular inflammation, ocular angiogenesis, rheumatoid arthritis (RA), atherosclerosis, inflammatory bowel diseases (IBD), asthma, chronic obstructive pulmonary disease, fever syndromes, cachexia, psoriasis, autoimmune diseases, cardiac diseases, retinoblastoma, cancer and/or any disorder associated with inflammation, immunomodulation and microbial infection.

BACKGROUND OF THE INVENTION

Sepsis was identified as one of the five conditions that account for the most expensive hospital stays in the United States. The outcome of sepsis is particularly unfavorable in elderly, immunocompromised, and critically ill patients. Besides its clinical challenge, the treatment of sepsis imposes a large economic burden on healthcare systems worldwide. With an estimated >900,000 cases occurring in the United States alone each year, the annual total costs have been estimated to be approximately $26 billion nationally. Currently, one of three broad adjunctive (nonantibiotic) therapy approaches are typically used to treat sepsis: (1) improving supportive care (i.e. oxygenation/ventilation strategies, optimization of fluid/vasopressor use, early goal-directed therapy); (2) targeting bacterial virulence factors (i.e. antiendotoxin antibodies, endotoxin removal columns); and (3) targeting host response factors (i.e. corticosteroids, anticytokine drugs, anticoagulants). However, current therapies are not completely effective in patients with sepsis and septic shock. These therapies are even less effective in immunocompromised and older patients.

BRIEF SUMMARY OF THE INVENTION

The present invention overcomes the drawbacks of the prior art by providing small molecular weight, water soluble, oligosaccharides (compounds 1-3) that exhibit antagonist activity against TLR4 useful for treating inflammatory disorders, such as age-related macular degeneration (AMD) pathogenesis. Such inflammatory conditions include, but are not limited to, ocular inflammatory diseases and choroidal neovascularization. Specifically, the present invention relates to compounds (4, 15, 16 and 25) for the treatment of inflammation. In some embodiments the inflammation may be caused by polymicrobial infections. In some embodiments the compounds find use in the treatment of sepsis and severe sepsis, SIRS and septic shock.

Compounds of the present invention have been unexpectedly found to possess superior anti-inflammatory activity in inhibiting inflammatory biomarkers such as TNF-α, IL-1β and IL-6 in LPS induced human monocyte assay and producing anti-inflammatory cytokine IL-10 in monocytes. Compounds of present invention protected mice from both lethal gram negative sepsis against *Escherichia coli* and polymicrobial sepsis in a cecal ligation and puncture model. Accordingly, the present disclosure provides methods of inhibiting inflammatory biomarkers such as, but not limited to, TNF-α, IL-1β and IL-6 in LPS induced human monocyte assay by administering the compounds disclosed herein to a patient in need thereof. In addition the present disclosure provides methods of protecting mice from lethal gram negative sepsis against Escherichia coli by administering the compounds disclosed herein to a patient in need thereof. Compounds of the present invention have also been unexpectedly found to possess broad spectrum antimicrobial activity against both gram positive (methicillin susceptible *Staphylococcus aureus* and methicillin resistant *Staphylococcus aureus*), gram negative (*E. Coli, P. aeruginosa, A. baumannii, K. pneumonia*) bacteria as well as fungus (*C. albicans*) mostly found in burn and septic wounds. Accordingly, the present disclosure provides methods of treating infection caused by both gram positive (methicillin susceptible Staphylococcus aureus and methicillin resistant Staphylococcus aureus), gram negative (*E. coli, P. aeruginosa, A, baumannii, K pneumonia*) bacteria as well as fungus (*C. albicans*) by administering compounds disclosed herein to a patient in need thereof. Compounds of the present invention have also been unexpectedly found to inhibit and eradicate biofilm formed by *S. aureus*. Accordingly, the present disclosure provides methods of inhibiting or eradicating biofilm formed by a microorganism, such as but not limited to *S. aureus* by contacting a surface with compounds disclosed herein. Compounds of present invention also demonstrated superior in vivo efficacy in protecting mice against cecal ligation and puncture (CLP) induced death and organ dysfunction. Compounds of the present invention have also been unexpectedly found to possess superior activity against HMGB1 induced inflammation in mouse macrophages and reduced VEGF expression in retinal pigmental epithelial cells (ARPE-19) and daily intraperitoneal injection of the compound was able to reduce the average size of CNV lesions to about 60% of those in control mice treated with vehicle only. Accordingly, the disclosure provides methods of protecting a subject in need thereof from infection or disorders associated with infection by treating said subject with a compound as disclosed herein.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying figures. However, figures provided herein are intended to help illustrate the invention or assist with developing an understanding of the invention, and are not intended to be definitions of the invention's scope.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 14 demonstrates that compounds of present invention inhibited biofilm formation.

DETAILED DESCRIPTION OF THE INVENTION

Figure 1:
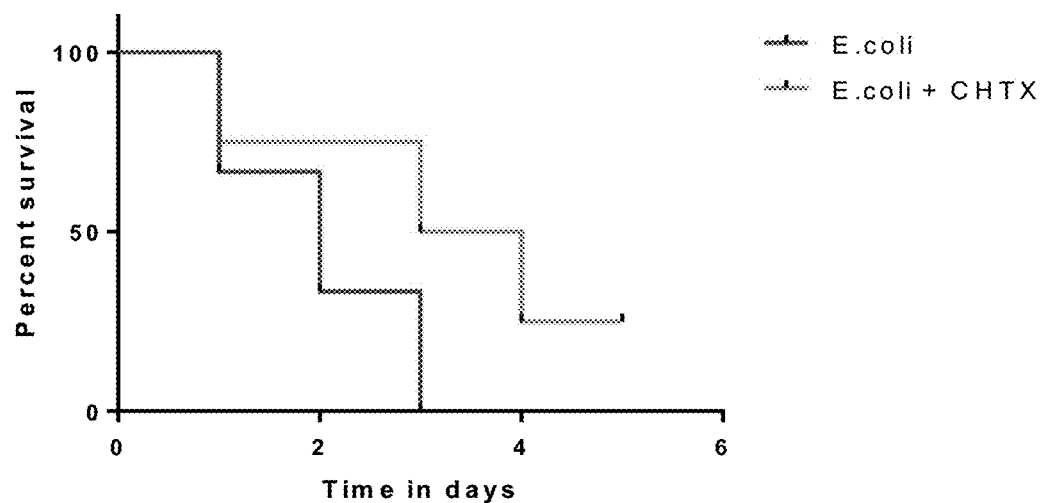
FIG. 1 is a graph showing the results of an evaluation of the TLR4 antagonist compound 1 of the present invention in a mouse endotoxemia sepsis model and illustrates that compound 1 protected mice from lethal gram negative sepsis against *E. coli*.

In sepsis caused by gram-negative bacteria, lipopolysachharide (LPS) activates the immune system through signaling receptor Toll Like Receptor 4 (TLR4) to initiate the process for production of inflammatory cytokines (TNF-α, IL-1β, IL-6, ROS) responsible for hyper-inflammation. Thus, some investigators are seeking to develop antagonists that block either activation through TLRs or downstream signaling pathways that inhibit the storm of inflammatory molecules. However, no target molecule has progressed beyond experimental and preclinical work, except Eritoran, a LPS analog which failed in clinical trial with possible reason of poor clinical study design [Opal et al, JAMA, 309, 1154-1162 (2013)]. The underlying mechanism of action for most other class of compounds is not completely understood [Leon, et al., Pharm. Res. 25(8):1751-1761 (2008); Athina and Thierry, Frontiers in Immunology 4387 (2013)].

The compounds of present innovation are small molecules that can synergistically inhibit inflammation microbial infection and upregulate M2 biomarker such as IL-10 with therapeutic potential to treat sepsis, septicemia and septic shock.

Posterior segment neovascular ocular diseases, as exemplified by proliferative diabetic retinopathy (PDR), exudative age-related macular degeneration (AMD) and retinopathy of prematurity (ROP), are a growing and huge health threat which require new effective therapies. Retinal neovascularization associated with PDR is the leading cause of blindness in working age adults. Choroidal neovascularization (CNV) is responsible for 200,000 new cases of exudative AMD each year in the US rendering this neovascular pathology the leading cause of legal blindness in non-third world nations. The projected number of people with AMD in 2020 is 196 million, increasing to 288 million in 2040 [Wong et al, *The Lancet Global Health* 2014, 2, e106-e116]. Pathological angiogenesis associated with ROP is the major cause of blindness in children under the age of seven [Harrell et al, *Neonatal Network* 2007, 26, 371-378].

Multiple lines of evidence suggest that Toll Like Receptor (TLR4) signaling may be associated with pathologic changes in retinal diseases [Cho et al, *Investigative Ophthalmology & Visual Science* 2009, 50, 5614-5618], including AMD eyes by oxidized lipids, lipofuscin and by drusen components. Once activated, TLR4 could contribute to the pathogenesis of AMD by multiple mechanisms such as release of TNF-α, interleukin-1β, and other pro-inflammatory mediators. TLR4 activation suppresses Wnt signaling, leading to reduced growth factor expression, secretion, and increased photoreceptor death in response to oxidative stress as well as can also lead to oxidative damage of photoreceptor outer segments. TLR4 has a direct effect on several inflammation-related signaling pathways including MAPK, NFκ-13 and Jak1/Stat1 and shown to mediate neuronal toxicity through caspase-3, neuronal iNOS and ERK1/2, JNK1/2 and p38. Interestingly, TLR4-mediated microglial activation by endogenous photoreceptor proteins in retinal inflammation can aggravate retinal cell death. Finally, release of high-mobility group box-1 in ischemic neural tissue has been shown to initiate TLR4-dependent responses that contribute to retinal neovascularization [He et al, Arteriosclerosis, Thrombosis, and Vascular Biology. 2013;33: 330-338].

Accordingly, there exists a need for more effective treatments for inflammation and in particular for both dry and wet AMD pathogenesis. The compounds and methods described herein, therefore demonstrated that inhibition of TLR4 activity is of therapeutic value in AMD and other retinal diseases. The compounds of present innovation are small molecules that can synergistically inhibit angiogenesis, inflammation and accelerate phagocytosis with therapeutic potential to treat AMD.

Prior to the present disclosure, however, it does not appear that there are any reports published on the use of chitohexaose (compound 1), chitohepatose (compound 2) and chitooctaose (compound 3) and derivatives thereof as TLR4 antagonist for inhibiting inflammation and angiogenesis for ocular indications such as dry/wet AMD, diabetic retinopathy, or any chronic ocular inflammation.

In one embodiment, the principles of the present disclosure provide a compound of Formula (I):

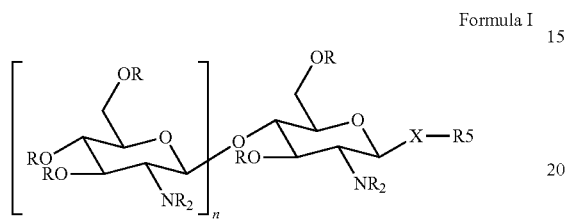

Formula I where:

R=H, C(O)R$_1$, alkyl, benzyl, substituted benzyl

R$_1$=CH$_3$, alkyl, piperidine nitroxyl

R$_2$=H, C(O)R$^1$ or aceloxy alkyl carbamate of the following formula

R$_2$=C(O)OCHR$_3$OC(O)OR$_4$, piperidine nitroxyl

R$_3$=H, CH$_3$, C$_2$H$_5$, Isopropyl

R$_4$=optimally substituted alkyl group

X=O, NH, S

R$_5$=alkyl, cycloalkyl, aryl, substituted aryl, heteroaryl, heteroalkyl, heterocycloalkyl, piperidine nitroxyl, piperidine N-hydroxylamine n=0-7

In another embodiment, the present disclosure provides a compound of Formula (II):

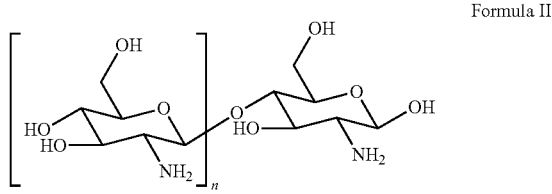

Formula II where:

a. n=2-7

Additional compounds of the present disclosure include the following structures shown below:

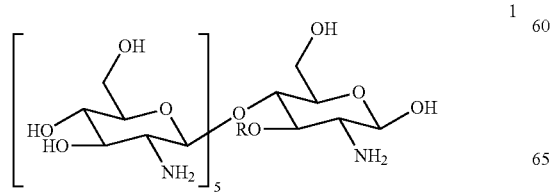

1

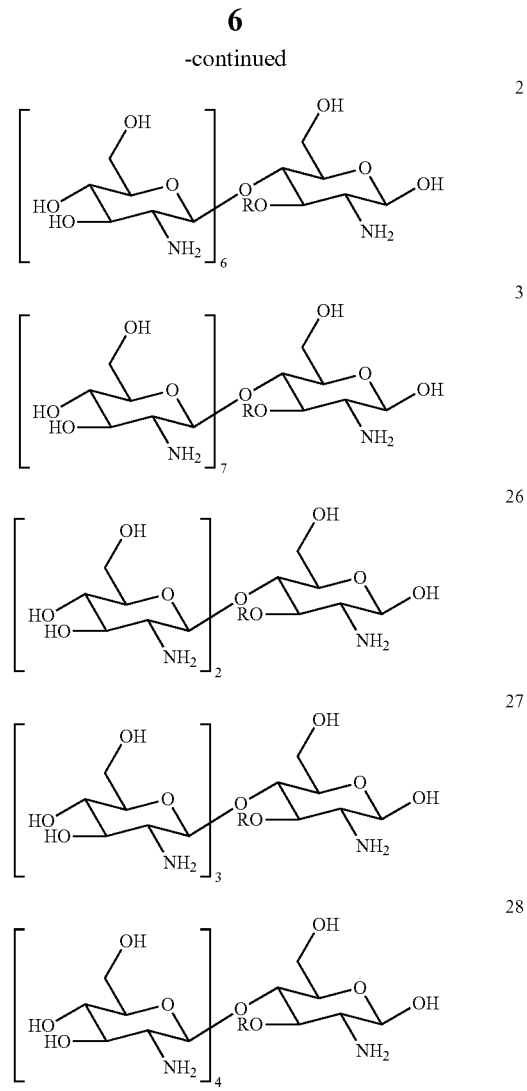

Figure 19:
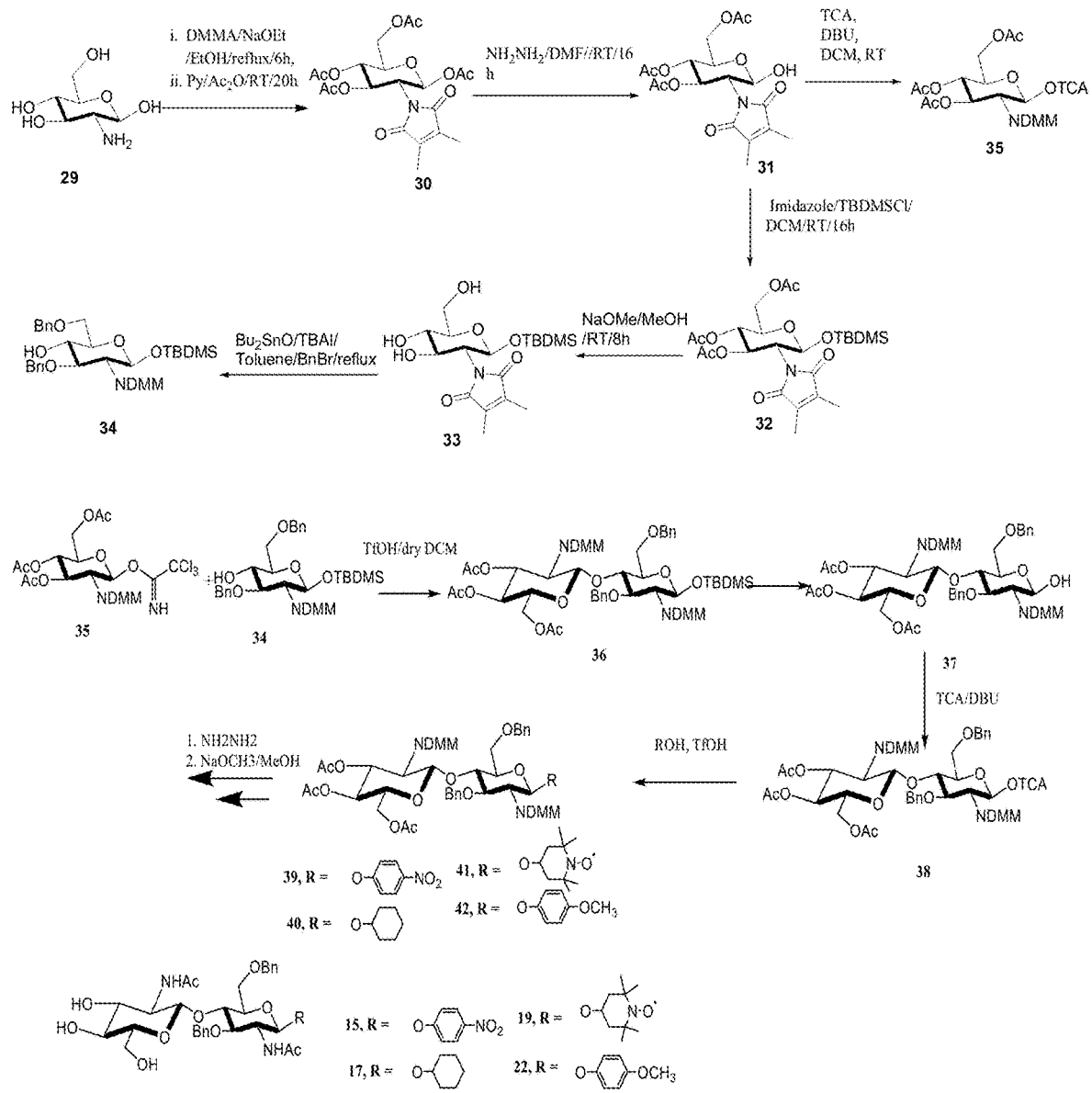
FIG. 19 provides the synthetic scheme for preparing compounds 22-23.
Figure 20:
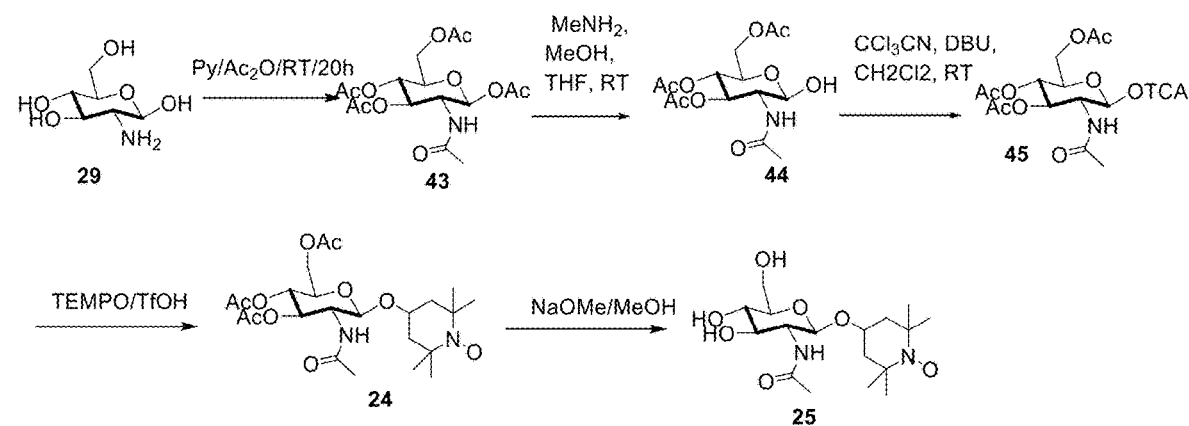
FIG. 20 provides the synthetic scheme for preparing compounds 24-25.

Compounds of the present disclosure (2, 3) have shown unexpectedly potent activity in inhibiting LPS and HMGB1 induced inflammation biomarkers (TNF-α, IL-1β and IL-6) in bone derived mouse macrophages as well as in human monocytes. Compounds 1 and 2 decrease the production of VEGF in ARPE-19 cells. Compound 2 showed significant decrease in CNV size in lased induced mice model for wet AMD. Compounds of the present invention (1-3) can be synthesized using the synthesis schemes illustrated in FIG. 19 in conjunction with knowledge available in the prior art and may be modified as needed:

In another embodiment, the present invention provides a compound of Formula (III):

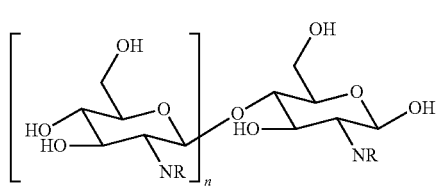

Formula III where:
n=0-5
R=COR$_1$
R$_1$=CH$_3$, alkyl,

Additional compounds of the present invention include the following structures shown below:

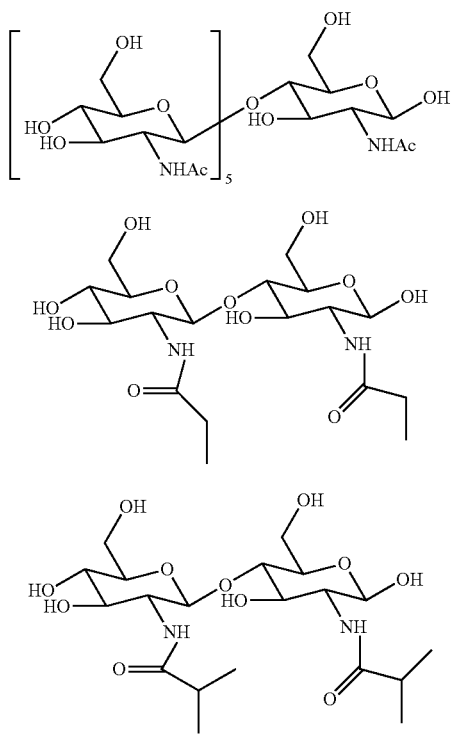

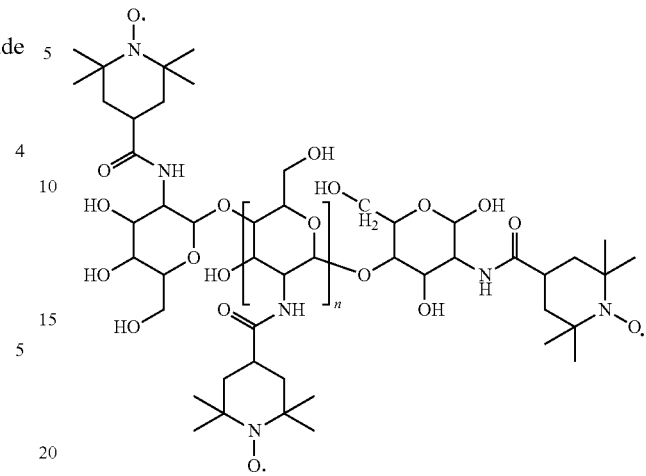

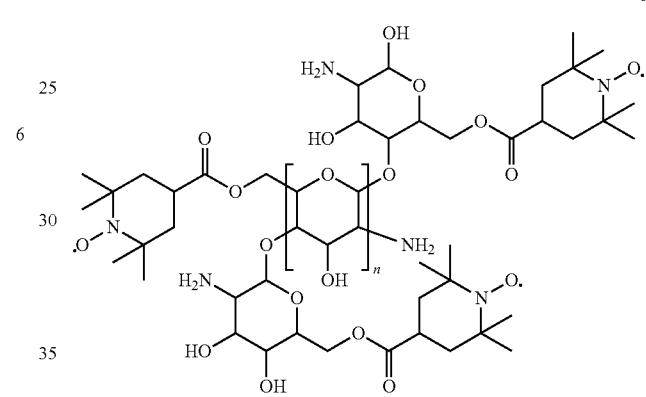

Figure 2:
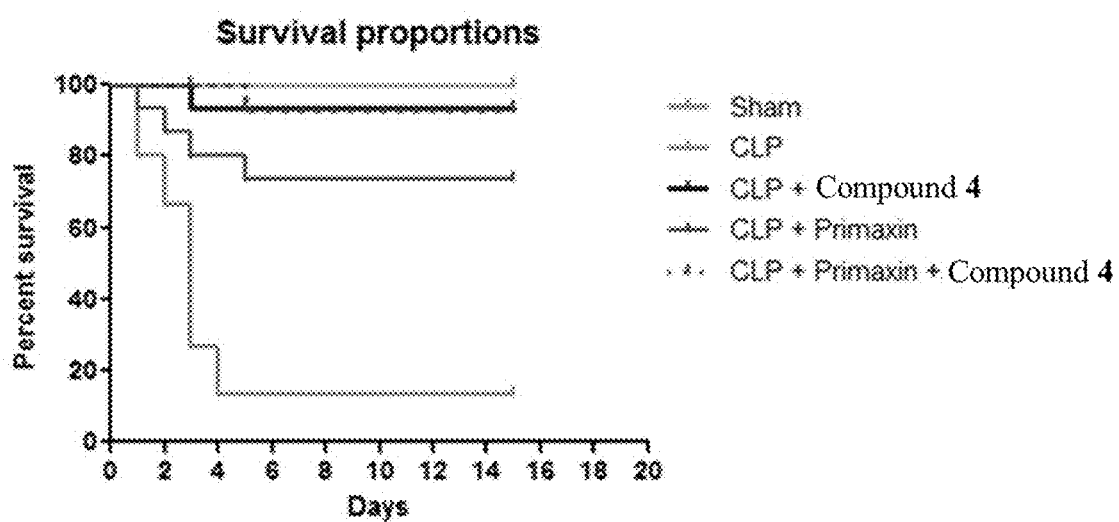
FIG. 2 is a graph showing the results of an evaluation of the TLR4 antagonist compound 4 of the present invention in a cecal ligation and puncture (CLP) model and illustrates that compound 4 protected mice from CLP induced polymicrobial sepsis and death.
Figure 3:
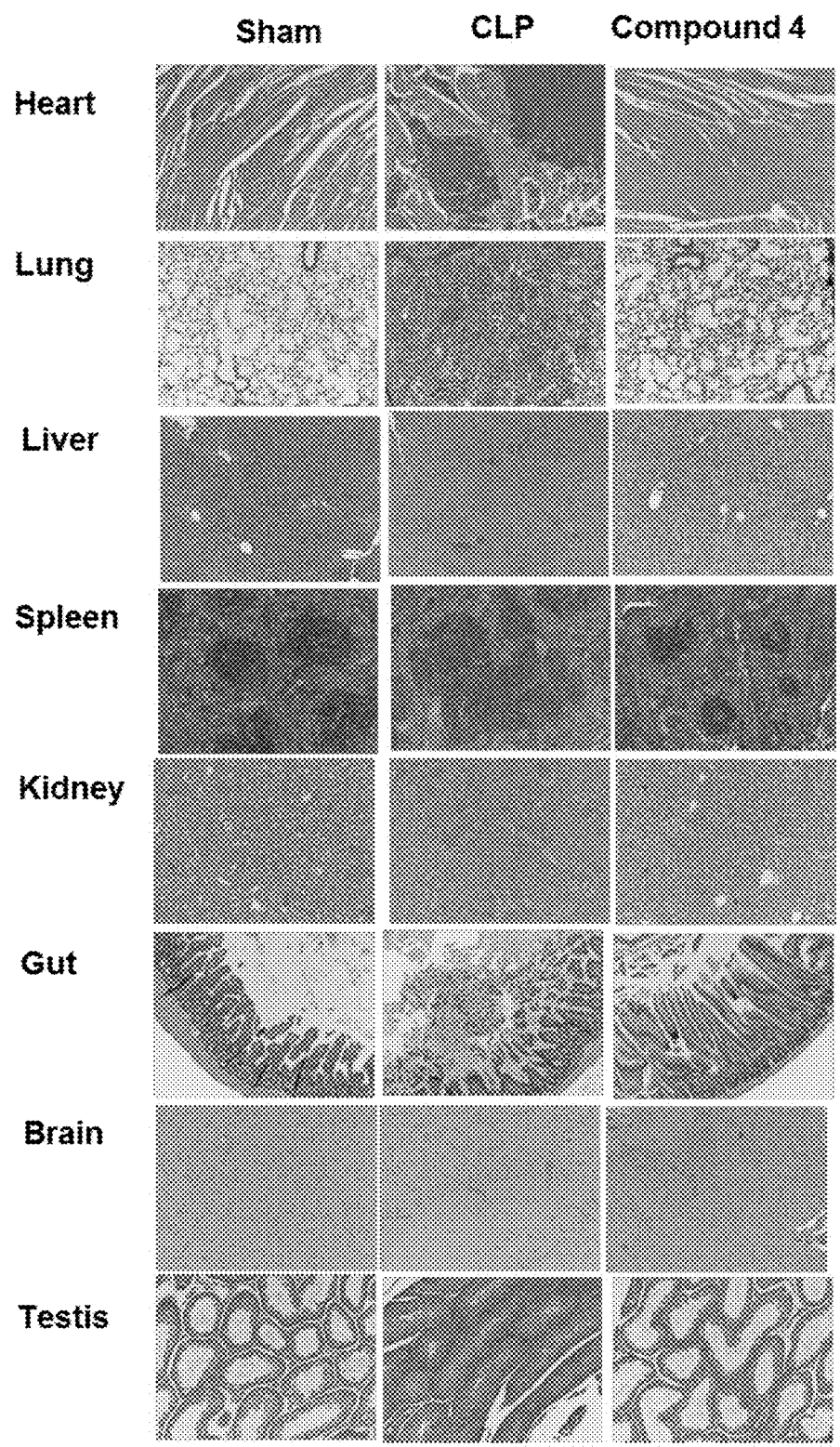
FIG. 3 is the histopathology of major organs which demonstrates that, on treatment of compound 4, a compound of present invention reversed the major pathological changes and tissues resembled to sham group.
Figure 4:
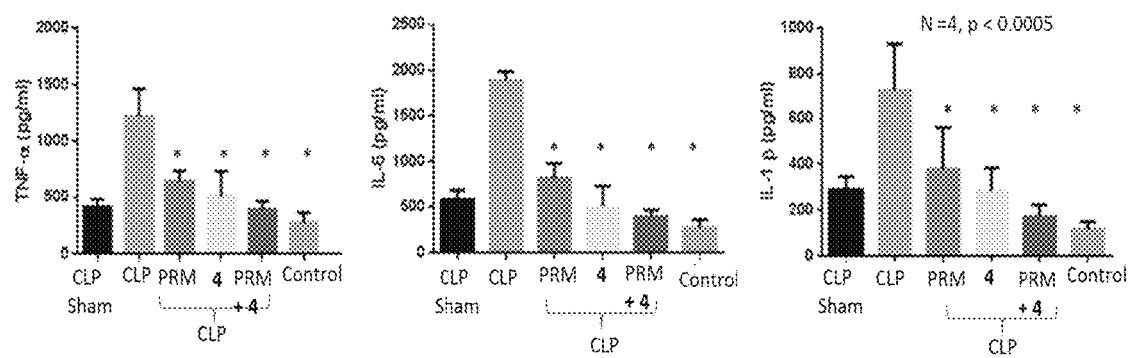
FIG. 4 demonstrated that compound 4 of present invention effectively down regulates the inflammatory cytokines in vivo in CLP mice.

Compounds of the present invention (4) have shown unexpectedly superior activity in inhibiting LPS induced inflammation biomarkers (TNF-α, IL-1β and IL-6) in human monocytes. As illustrated in FIGS. 2-4, Compound 4 demonstrated high efficacy in protecting organ dysfunction and death of mice in a cecal ligation and puncture (CLP) model of sepsis at 10 mg/kg on intravenous (IV) dosing and downregulated inflammatory cytokines such as TNF-α, IL-1β and IL-6 in a statistically significant manner.

Compounds of the present invention (4-6) can be synthesized using reported procedure as describe in Mohamed R. E et al, Carbohydrate research, 2001, 331, 129-142.

In another embodiment, the present invention provides a compound of Formula (IV): 1.

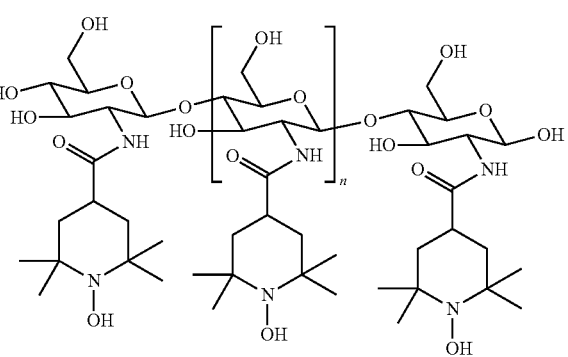

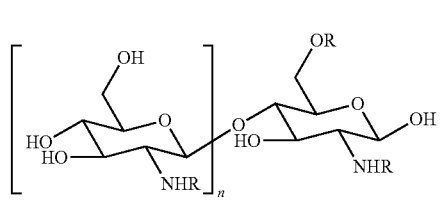

where:
R=H and C(O)R$^1$
R$^1$=piperidine nitroxyl or piperidine N-hydroxyl amine
n=0-7

Additional compounds of the present invention include the following structures shown below:

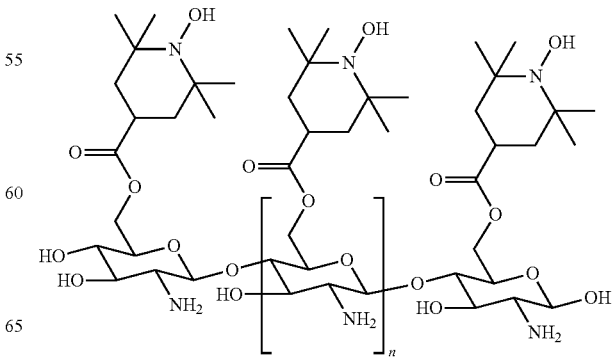

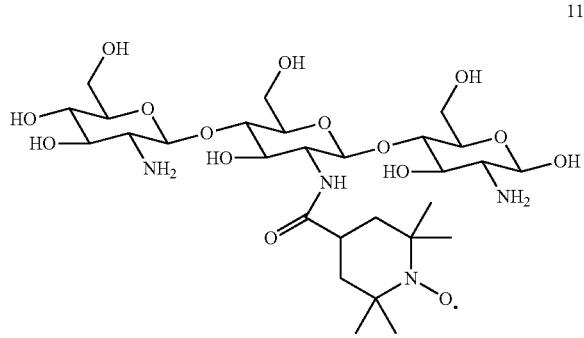

11

Figure 18:
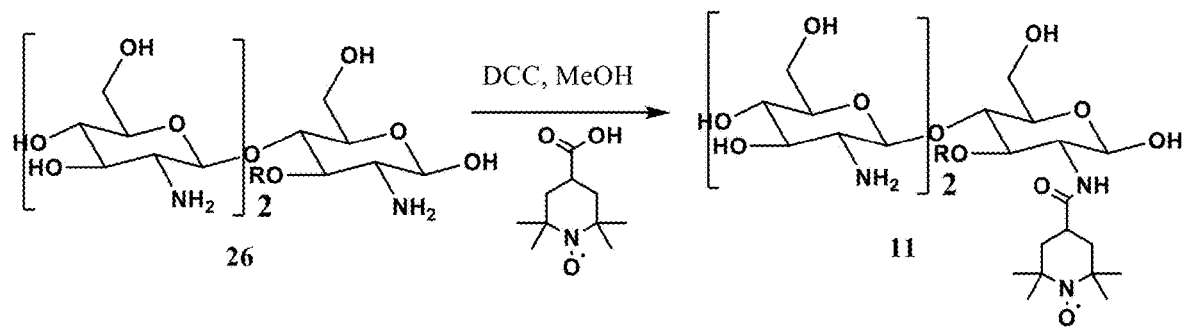
FIG. 18 shows the synthetic scheme for preparing compound 11.

Compounds of the present invention (11) have shown unexpectedly superior activity in inhibiting LPS induced inflammation biomarkers (TNF-α, IL-1β and IL-6) in human monocytes. Accordingly, the compounds find use as anti-inflammatory compounds. Compounds of the present invention (7-11) can be synthesized using the synthesis schemes illustrated in FIG. 18 in conjunction with knowledge available in the art.

In another embodiment, the present invention provides a compound of Formula (V):

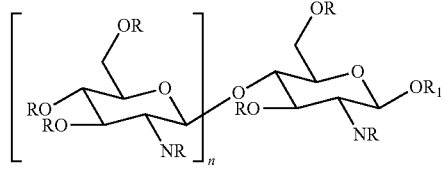

Formula V where:
n=0-5
R═H, C(O)CH$_3$, C(O)-piperidine nitroxy, C(O)-piperidine N-hydroxyl
R$_1$=alkyl, cycloalkyl, aryl, substituted aryl, heteroaryl, piperidine nitroxyl, piperidine N-hydroxyl Additional compounds of the present invention include the following structures shown below:

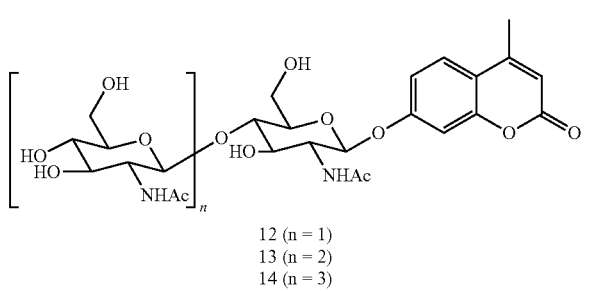

12 (n = 1)
13 (n = 2)
14 (n = 3)

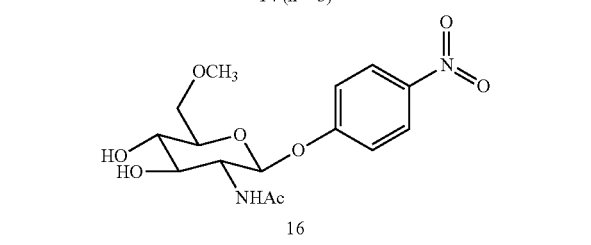

16

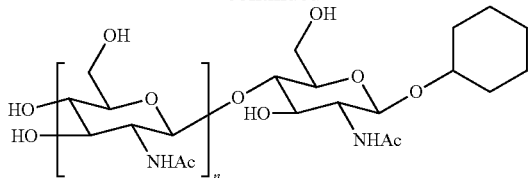

18 (n = 3)

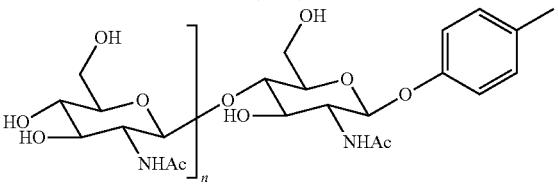

20 (n = 0)
21 (n = 3)

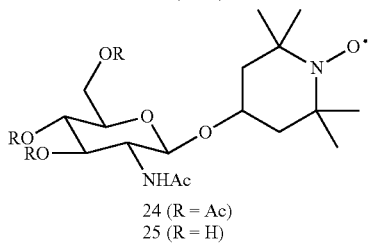

24 (R = Ac)
25 (R = H)

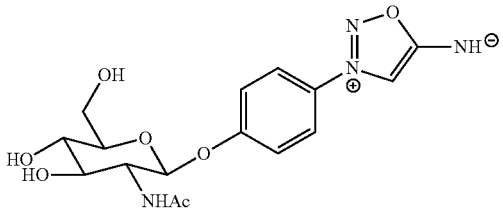

Compounds of the present invention (12-25) have shown to inhibit LPS induced inflammation biomarkers (TNF-α, IL-1β and IL-6) in human monocytes and upregulated anti-inflammatory cytokine, M2 biomarker IL-10. Compound 12 also showed broad spectrum antimicrobial activity against gram negative, gram positive bacteria as well fungus. Compound 12 unexpectedly inhibited biofilm formation by MSSA and MRSA. Compound 25 demonstrated high survival, organ protection in CLP mice model of sepsis when administered intravenously (10 mg/kg dose). Accordingly, compounds as described herein find use as anti-inflammatory molecules in some embodiments. In some embodiments the compounds are anti-infective or antimicrobial.

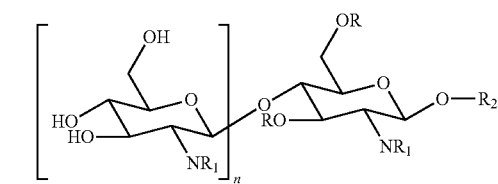

Formula-VI where:
n=0-1
R=benzyl, substituted benzyl
R$_1$═COCH$_3$, N-dimethylmaleimide
R$_3$=cyclohexyl, p-nitro phenyl, piperidine nitroxy, piperidine-N-hydroxyl, p-methoxy phenyl.

Additional compounds of the present invention include the following structures shown below:

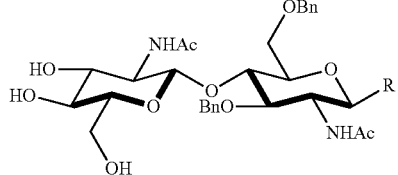

15, R = 

17, R = 

19, R = 

22, R = 

39

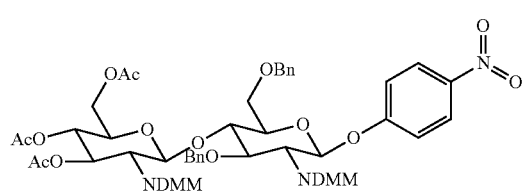

40

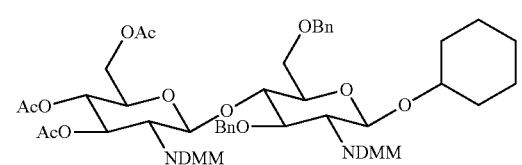

41

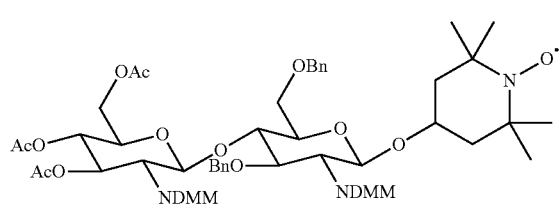

42

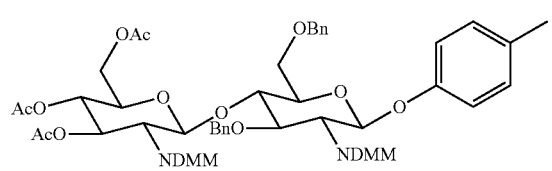

43

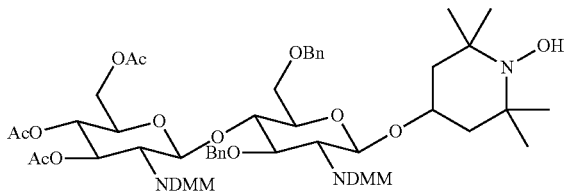

Compounds of the present invention have shown to inhibit LPS induced inflammation biomarkers (TNF-α, IL-1β and IL-6) in human monocytes and upregulated IL-10. Compounds 15 also showed broad spectrum antimicrobial activity against gram negative, gram positive bacteria as well fungus. Compounds 15 unexpectedly inhibited biofilm inhibition by MSSA and MRSA. Compound 15 demonstrated high survival, organ protection in CLP mice model of sepsis when administered intravenously (5.0 mg/kg dose). Compounds of the present invention can be synthesized using the synthesis schemes illustrated in FIG. 19 developed by us in conjunction with knowledge available in the art.

Furthermore, certain embodiments comprise pharmaceutically acceptable salts of compounds according to the present invention. Pharmaceutically acceptable salts comprise, but are not limited to, soluble or dispersible forms of compounds according to the present invention that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

FORMULATIONS

In some embodiments, the compounds of the present disclosure are incorporated into parenteral formulations. The term parenteral as used herein includes subcutaneous, intravenous, intramuscular, and intra-arterial injections with a variety of infusion techniques. Intra-arterial and intravenous injection as used herein includes administration through catheters. Preferred for certain indications are methods of administration that allow rapid access to the tissue or organ being treated, such as intravenous injections for the treatment of endotoxemia or sepsis.

The compounds of the present disclosure will be administered in dosages which will provide suitable inhibition of LPS activation of target cells; generally, these dosages are, preferably between 50-3000 mg/patient, or from 100-2500 mg/patient or from 200-2000 mg/patient or from 500-1000 mg/patient or from 750-1000 mg/patient, more preferably, between 500-750 mg/patient and most preferably, between 250-500 mg/patient. The dosages are preferably once a day for 28 days, more preferably twice a day for 14 days or most preferably 3 times a day for 7 days.

Pharmaceutical compositions containing the active ingredient may be in any form suitable for the intended method of administration.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenteral-acceptable diluent or solvent, such as a solution in 1,3-butanediol or prepared as a lyophilized powder, Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments the formulation comprises PLA or PLGA microparticles and may be further mixed with $Na_2HPO_4$, hydroxypropyl methylcellulose, polysorbate 80, sodium chloride, and/or edentate disodium.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

It will be understood, however, that the specific dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

In some embodiments the compositions of the present disclosure also contain from about 80% to about 99.5%, preferably from about 90 or 95% to about 98.5% of a compatible non-aqueous pharmaceutically acceptable topical vehicle. Some vehicles are described in U.S. Pat. No. 4,621,075, which is incorporated herein for this disclosure. Although it is preferred that these vehicles be free of water, the compositions of the present invention may contain up to about 5% water without significant adverse effects on the formation of the desired gels. These non-aqueous vehicle components are also well-known in the pharmaceutical arts, and they include (but are not limited to) short chain alcohols and ketones and emollients, such as hydrocarbon oils and waxes, lanolin and lanolin derivatives, silicone oils, monoglyceride, diglyceride, and triglyceride esters, fatty alcohols, alkyl and alkenyl esters of fatty acids, alkyl and alkenyl diesters of dicarboxylic acids, polyhydric alcohols and their ether and ester derivatives; wax esters and beeswax derivatives. Preferred vehicles incorporate methanol, ethanol, n-propanol, isopropanol, butanol, polypropylene glycol, polyethylene glycol and mixtures of these components. Particularly preferred vehicles include ethanol, n-propanol and butanol, especially ethanol. These preferred solvents may also be combined with other components, such as diisopropyl sebacate, isopropyl myristate, methyl laurate, silicone, glycerine and mixtures of these components, to provide non-aqueous vehicles which are also useful in the present invention. Of these additional components, diisopropyl sebacate is especially useful. In fact, preferred vehicles include mixtures of ethanol and diisopropyl sebacate in ratios, by weight, of from about 4:1 to about 1:4. Preferred vehicles contain from about 15% to about 35% diisopropyl sebacate and from about 65% to about 85% ethanol.

Compositions of the present invention may additionally contain, at their art-established usage levels, compatible adjunct components conventionally used in the formulation of topical pharmaceutical compositions. These adjunct components may include, but are not limited to, pharmaceutically-active materials (such as supplementary antimicrobial or anti-inflammatory ingredients, e.g., steroids) or ingredients used to enhance the formulation itself (such as excipients, dyes, perfumes, skin penetration enhancers, stabilizers, preservatives, and antioxidants). Since the compositions of the present invention permit the formation of gels without requiring the presence of conventional gelling agents, such agents are preferably not included. Examples of such agents include the pharmaceutically-acceptable acidic carboxy polymers, such as the Carbopol compounds commercially available from B. F. Goodrich Chemicals, Cleveland, Ohio.

The gel-form compositions of the present invention may be formulated by the conventional mixing of the components described above. Gel formation takes place within from about 2 minutes to about 16 hours after mixing, depending upon the components utilized.

In one embodiment the cream, lotion or gel packaged in a common trigger spray container will be firmly adhered to the area of interest as a regular cream does after it is sprayed out from the container. This is described in WO 98/51273, which is incorporated herein by reference. Accordingly, in one aspect, the present disclosure provides a pharmaceutical non-aerosol spray composition for topical application, which comprises the compounds as described herein alone or in combination. The compounds are present in an amount in the range of 0.1% to 20% or in some embodiments from 1 to 15% by weight, or in some embodiments from 2 to 10% by weight of cream, lotion or gel. The compounds used in the present invention can be incorporated into a neutral hydrophilic matrix cream, lotion or gel. In a first preferred embodiment, the cream or lotion matrix for topical application is characterized by polyoxyethylene alkyl ethers. In a second preferred embodiment, the gel is characterized by high molecular weight polymer of cross-linked acrylic acid. Polyoxyethylene alkyl ethers are non-ionic surfactants widely used in pharmaceutical topical formulations and cosmetics primarily as emulsifying agents for water-in-oil and oil-in-water emulsions. It is characterized in this invention as a base for non-aerosol trigger sprayable cream or lotion. Cross-linked acrylic acid polymer (Carbomer) employed to form the gel is another object of this invention.

A particularly suitable base for non-aerosol spray is therefore a cream or lotion containing from 1 to 25% of polyoxyethylene alkyl ethers, 3 to 40% of humectant and 0.1 to 1% of preservative or preservatives and the balance to 100% being purified water. Apply the polyoxyethylene alkyl ether can be one or any combination selected from the group consisting of polyoxyl 20 cetostearyl ether (Atlas G-3713), poloxyl 2 cetyl ether (ceteth-2) poloxyl 10 cetyl ether (oleth-10), poloxyl 20 cetyl ether (ceteth-20), poloxyl 4 lauryl cetyl ether (laureth-4), poloxyl 23 lauryl cetyl ether (laureth-23), poloxyl 2 oleyl ether (oleth-2), poloxyl 10 oleyl ether (oleth-10), poloxyl 20 oleyl ether (oleth-20), poloxyl 2 stearyl ether (steareth-2), poloxyl 10 stearyl ether (steareth-10), poloxyl 20 stearyl ether (steareth-20) and poloxyl 100 stearyl ether (steareth-100). Suitable humectant can be one or any combination selected from the group consisting of propylene glycol, polyethylene glycol, sorbitol or glycerine. Suitable preservative is one or any combination selected from the group consisting of methylparaben, propylparaben, benzyl alcohol, benzoic acid, sodium benzoate, sorbic acid and its salt or phenylethyl alcohol.

Another suitable base for non-aerosol spray is a gel containing from 0.1 to 2.0% of Carbomer, 0.1 to 1% of alkaline solution, 3 to 40% of humectant and 0.1 to 1% of preservative or preservative as and the balance to 100% being purified water. Aptly the Carbomer can be one or any combination selected from the group consisting of Carbomer 934, Carbomer 940 or Carbomer 941, The suitable humectant, preservative and purified water for the gel are same as that in the case or cream or lotion. Other sprayable formulations are described in US Pre-Grant Publication U52005/00255048, which is expressly incorporated herein by reference.

Ophthalmic Formulation (Topical and Intravitrael Dosing):

The compound of the invention will typically be a small percentage of the total ophthalmic composition. The compound of the invention will typically be at least 0.01 w/v %, more typically at least 0.1 w/v % and even more typically at least 0.5 w/v % of the ophthalmic composition. The compound of the invention will also typically be no greater than 5.0 w/v %, even more typically no greater that 3.0 w/v % and even more typically no greater than 1.5 w/v % of the ophthalmic composition.

The ophthalmic composition will also typically include a suitable ophthalmic vehicle for delivery of the compound to the eye. It is contemplated that the ophthalmic composition may be configured for topical or intravitrael application to the eye and the ophthalmic vehicle will likely be different depending upon the manner of application. Generally, for either topical or intravitrael applications, it is preferable that the ophthalmic composition be aqueous and include a substantial amount of water. Typically the composition will include at least 30 w/v %, more typically at least 80 w/v % and even more typically at least 90 w/v % water (e.g., purified water).

For intravitrael applications, particularly when the ophthalmic composition is applied to the eye with a syringe, the ophthalmic compositions may include only or consist essentially of water and compound of the invention. For sustained drug release, PLGA. or macroparticle formulation of the compound of invention will be used as described by Shelke et al [Drug Deliv Transl Res. 2011, (1): 76-90]. Of course the ophthalmic composition could include other ingredients as well such as $Na_2HPO_4$, hydroxypropyl methylcellulose, polysorbate 80, sodium chloride, and edentate di sodium.

It could also be the case that the vehicle be only or consist essentially of water for a topical application, particularly if that topical application is performed shortly after water is combined with the test compound or the composition is packaged in a manner to prevent contamination. However, if the ophthalmic composition is to be applied as a multi-dose ophthalmic composition over an extended period of time (e.g., as drops from an eye-dropper once, twice, thrice or more per day for multiple days), the ophthalmic composition will likely include additional ingredients such as antimicrobial or preservative agents or systems, surfactants, buffering agents, tonicity agents, anti-oxidants, viscosity-modifying agents any combinations thereof or the like.

For topical application, the compositions of the present invention typically include antimicrobial agent. Potential antimicrobial agents include, without limitation, hydrogen peroxide, chlorine containing preservatives such as benzalkonium chloride or others. According to a preferred aspect, however, the composition of the present invention is entirely or substantially free of any non-polymeric quaternary anti-microbial agents such as benzalkonium chloride (BAK). Most preferred antimicrobial agent in the pharmaceutical composition includes polymeric quaternary ammonium compound.

As used herein, the phrase "substantially free of" as it refers to an ingredient of the ophthalmic composition means that it is contemplated that the ophthalmic composition can be either entirely devoid of that particular ingredient or includes only a nominal amount of that particular ingredient.

The polymeric quaternary ammonium compounds useful in the compositions of the present invention are those which have an antimicrobial effect and which are ophthalmically, acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.), which are expressly incorporated herein by reference. The most preferred polymeric ammonium compound is polyquaternium 1, otherwise known as POLYQUAD™ or ONAMERM™ with a number average molecular weight between 2,000 to 30,000. Preferably, the number average molecular weight is between 3,000 to 14,000.

The polymeric quaternary ammonium compounds are generally used in the suspensions of the present invention in an amount that is greater than about 0.00001 w/v %, more typically greater than about 0.0003 w/v % and even more typically greater than about 0.0007 w/v % of the suspension. Moreover, the polymeric quaternary ammonium compounds are generally used in the compositions of the present invention in an amount that is less than about 3 w/v %, more typically less than about 0.003 w/v % and even more typically less than about 0.0015 w/v % of the composition.

The antimicrobial agent of the composition of the present invention can additionally or alternatively include an antimicrobial system such as a borate/polyol complex system. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/ volume percentages of the ingredients polyol and borate include those amounts whether as part of a complex or not.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids, Preferred polyols are sugars, sugar alcohols and sugar acids, including, but not limited to: mannitol, glycerin, xylitol, sorbitol and propylene glycol.

When used, the borate/polyol complex antimicrobial system (i.e., the borate and polyol together) typically comprise at least 0.05 w/v %, more typically at least 0.5 w/v % and even possibly at least 1 or even at least 1.2 w/v % of the composition and also typically comprise less than 5 w/v %, more typically less than 2.2 w/v % and even possibly less than 1.6 w/v % of the composition. The borate to polyol ratio (weight to weight ratio) in the composition is typically between 1 to 1 and 1 to 10 and more typically is between 1 to 2 and 1 to 4 (e.g., about 1 to 3).

Tyloxapol, polysorbate-80 and polyoxyl hydrogenated castor oil are preferred surfactants. Tyloxapol is a highly preferred surfactant. When used, the surfactant is typically present in a concentration that is at least 0.01 w/v %, more typically at least 0.025 w/v % and even possibly at least 0.1 w/v % of the composition and also typically is less than 5 w/v %, more typically less than 2.0 w/v % and even possibly less than 1.0 w/v % of the composition.

The compositions of the present invention that are to be used for topical applications are typically formulated so as to be compatible with the eye. The ophthalmic compositions intended for direct application to the eye will be formulated so as to have a pH and tonicity that are compatible with the eye. The compositions will typically have a pH in the range of 4 to 9, preferably 5.5 to 8.5, and most preferably 5.5 to 8.0. Particularly desired pH ranges are 6.0 to 7.8 and more specifically 6.4 to 7.6, The compositions will have an osmolality of 200 to 400 or 450 milli osmoles per kilogram (mOsm/kg), more preferably 240 to 360 mOsm/kg.

Preferred compositions of the present invention are multi-dose ophthalmic compositions, for example, where the composition is in an eye dropper and can be administered as one or more drops once, twice, thrice or more times per day, topically to the eye. In that case, the compositions preferably have sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S, and other countries/regions are set forth in the following table:

| Preservative Efficacy Test ("PET") Criteria (Log Order Reduction of Microbial Inoculum Over Time) | Bacteria | Fungi |
| --- | --- | --- |
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

There are two preservative efficacy standards in the European Pharmacopoeia "A" and "B".

The standards identified above for the USP 27 are substantially identical to the requirements set forth in prior editions of the USP, particularly USP 24, USP 25 and USP 26.

As an added advantage, these ophthalmic compositions containing TLR4 antagonist compounds of the present invention are suitable for topical applications to the eye.

The formulations described herein may also contain additional active ingredients, such as but not limited to antimicrobial agents as described above, pain reducing agents and the like.

As such, once made, the compounds and formulations described herein find use in the treatment of a variety of ocular inflammatory disorders including, but not limited to, AMD, sepsis and severe sepsis, SIRS and septic shock and the like. The methods comprise administering to a patient in need thereof an effective amount of the antimicrobial and anti-inflammatory compositions described herein such that the disease or disorder is treated. The medical use of such compounds will be for the treatment and/or management of sepsis, neonatal sepsis, septicemia, septic shock, burn and wounds, infective endocarditis, biofilm inhibition, ocular infection, ocular inflammation, ocular angiogenesis, diabetic retinopathy, retinopathy of prematurity, uveitis, rheumatoid arthritis (RA), atherosclerosis, inflammatory bowel diseases (IBD), asthma, chronic obstructive pulmonary disease, broncho pulmonary dysplasia, fever syndromes, cachexia, psoriasis, autoimmune diseases, cardiac diseases, retinoblastoma, cancer and/or any disorder associated with inflammation, immunomodulation and microbial infection.

EXAMPLES

The following examples, including the experiments conducted and results achieved are provided for illustrative purposes only and are not to be construed as limiting the invention.

Example 1

Figure 6:
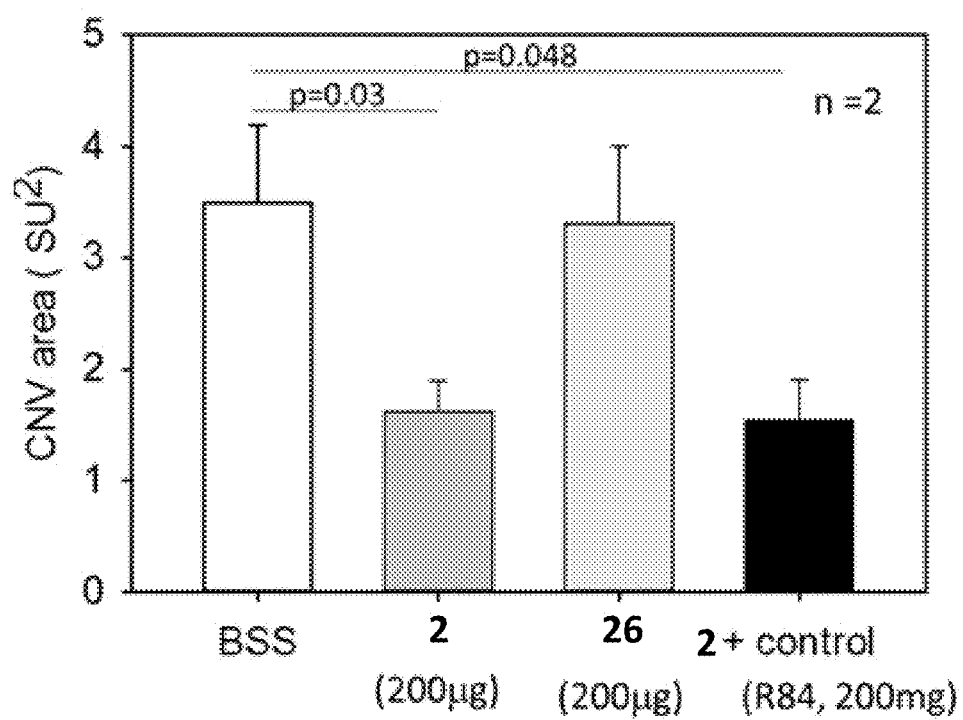
FIG. 6 demonstrates that an evaluation of the TLR4 antagonist compound 2 of the present invention in a lased induced CNV mouse model for wet AMD. Compound 2 decreased the choroidal neovascularization ~60% as compared to the positive control.
Figure 7A:
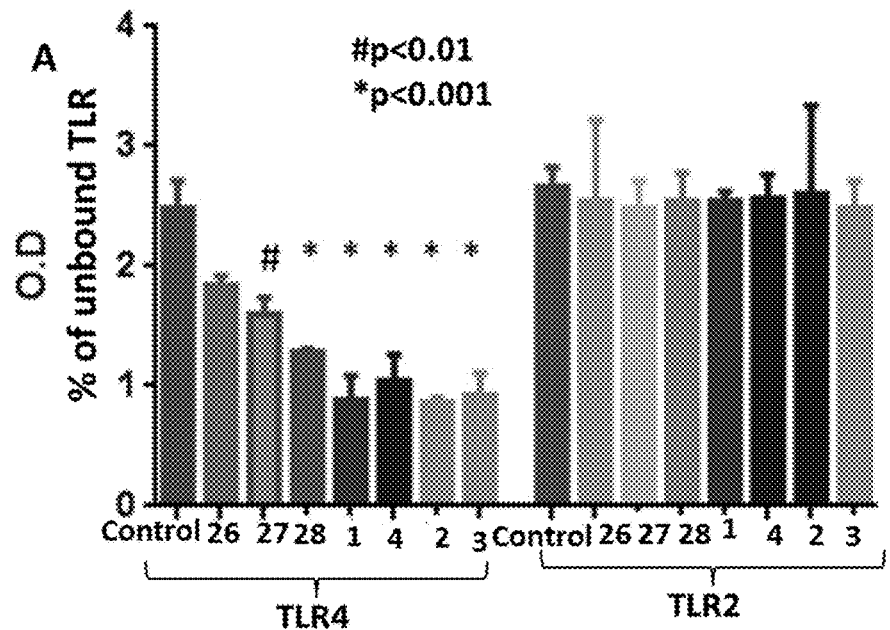
FIG. 7A and FIG. 7B demonstrate that a series of compounds of present invention binds to TLR4 receptor effectively and not to TLR2 receptor.
Figure 7B:
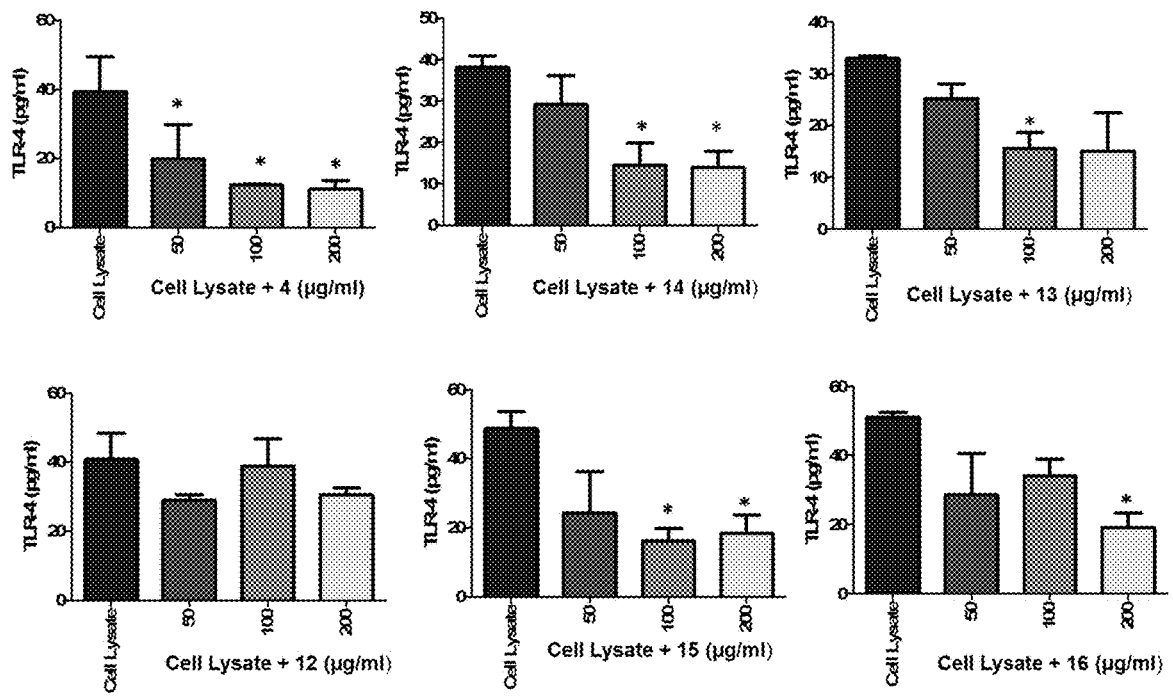

A Series of Compounds of Present Invention Binds to TLR4 Receptor Effectively and not to TLR2 Receptor ELISA plates were coated with human monocyte lysates (isolated from commercially available LeukoPak blood sample) followed by an array of compounds (10 µM) as shown in FIG. 6. It was then incubated with human monocyte lysates and then probed with anti-TLR4 and anti-TLR2 antibodies. Plates were developed using anti human IgG-HRP positive control. Compounds 1-3, binds to TLR4 receptor effectively and not to TLR2 receptor. Greater chain length analogs showed stronger antagonism (FIG. 7A). Similarly, other analogs were assessed for TLR4 antagonist assay as shown in FIG. 7B. Briefly, 0.5 million cells were grown in RPMI with 10% FBS O/N in two 24 well plate. Next day, the media was taken out without disturbing the lower layer and different concentration of compounds were added to make total amount of 0.5 ml volume with RPMI which was incubated for 48 hrs. Cells were harvested and the collected soup was analyzed using human TLR4 ELISA kit following manufacturer's instruction (Raybiotech).

Example 2

Figure 8A:
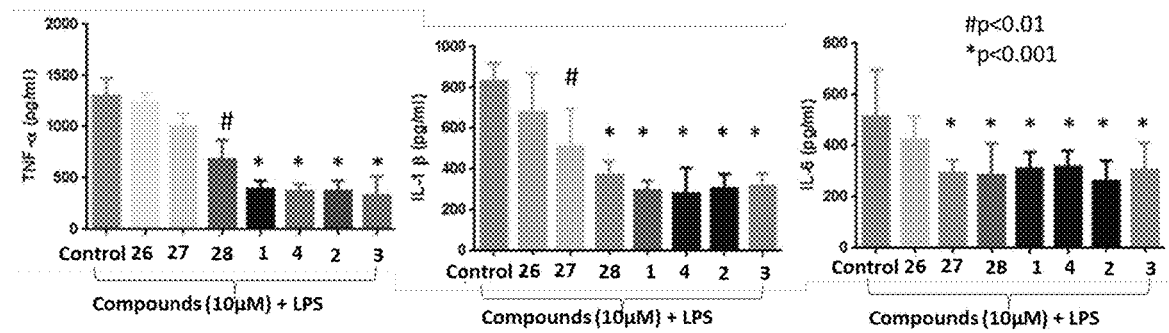
FIG. 8(A-B) demonstrates that compounds of present invention inhibited LPS induced production of inflammatory mediators in human monocytes.
Figure 8B:
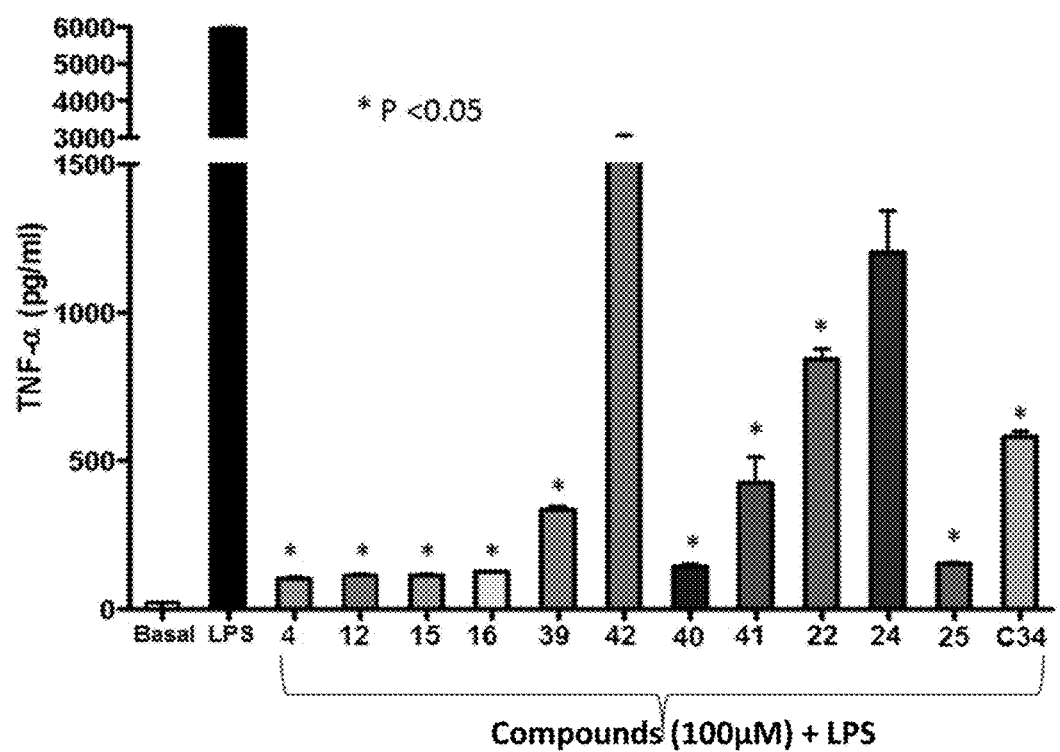

Compounds were Tested for Inhibiting the Production of Inflammatory Mediators in Human Monocytes To understand the structural requirement and limitations to probe the TLR4 binding pocket for optimal potency and efficacy, we have studied the ability of chitooligomers to inhibit LPS induced inflammation in human monocytes (FIG-8 A-B). Compounds 1-4 inhibited LPS induced cytokines TNF-α, IL-1β and IL-6) in a statistically significant manner at 10 µM concentration. Compound 2 and 4 (10 µM) were found to be more potent than chitohexaose, (Compound 1) (10 µM) in terms of percentage of inhibition of LPS mediated induction of inflammatory cytokines (LPS vs Chtx p<0.001 whereas LPS vs compound 2 or 4 p<0.0001). The protocol was followed as described [Panda etal, *PLoS Pathog* 2012, 8, e1002717]. Human monocytes were stimulated with LPS along with the series of compounds (10 µM) for 48 h. TNF-α, IL-1β, Il-6 in culture supernatants were quantified according to the manufacturer's instruction. Similarly, other analogs were assessed for their ability to inhibit LPS induced TNF-α production in human monocytes. Compounds 12, 15, 16, 39, 40, 41, 42, 25 were found to be potent inhibitor of TNF-α at 100 µM concentration (FIG. 8B).

Example 3

Figure 9:
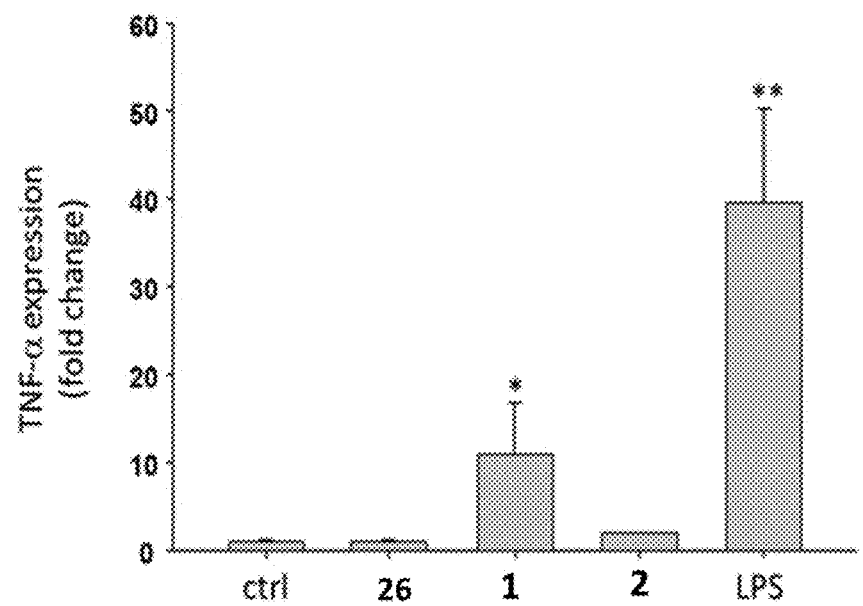
FIG. 9 demonstrates that compounds of present invention inhibits HMGB1 induced production of inflammatory mediator (TNF-α) in mouse bone marrow derived macrophages.

Compounds 1, 2, and 26 Inhibits LPS Induced Production of Inflammatory Mediator (TNF-α) in Mouse Bone Marrow Derived Macrophages Bone marrow derived mouse macrophages were treated with 100 µM of the above test compounds for 8 hours. Pro-inflammatory cytokines such as TNF-α protein level was measured by real-time RT-PCR. LPS treatment (10 ng/ml) was used as positive control (FIG. 9).

Example 4

Figure 10:
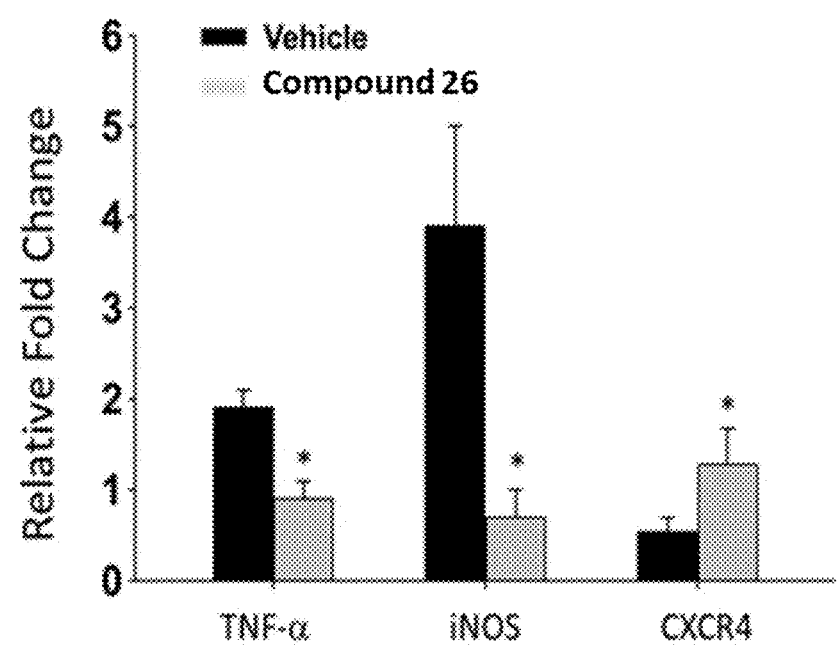
FIG. 10 demonstrates that compounds of present invention inhibits HMGB1 induced production of inflammatory mediators (TNF-α, i-NOS) and upregulate M2 biomarker CXCR4 in mouse macrophages.

Compound 26 Inhibits HMGB1 Induced Production of Inflammatory Mediators (TNF-α, i-NOS) and Upregulate M2 Biomarker CXCR4 in Mouse Macrophages The expressions of TNF-α and iNOS were both inhibited by compound 26 in macrophages. Interestingly CXCR4, an M2 macrophage marker, was upregulated by 26, suggesting potential effects on microphage polarization suggesting immune modulating activity. Bone derived macrophages from mouse were treated with HMGB1 for 8 hours, with or without 100 µM of compound 26. The mRNA levels of TNF-α, iNOS and CXCR4 were measured by real-time RT-PCR, and normalized to the expression level in control cells (FIG. 10).

Example 5

Compounds of Present Invention Produces Anti-Inflammatory Cytokines IL-10

Figure 11:
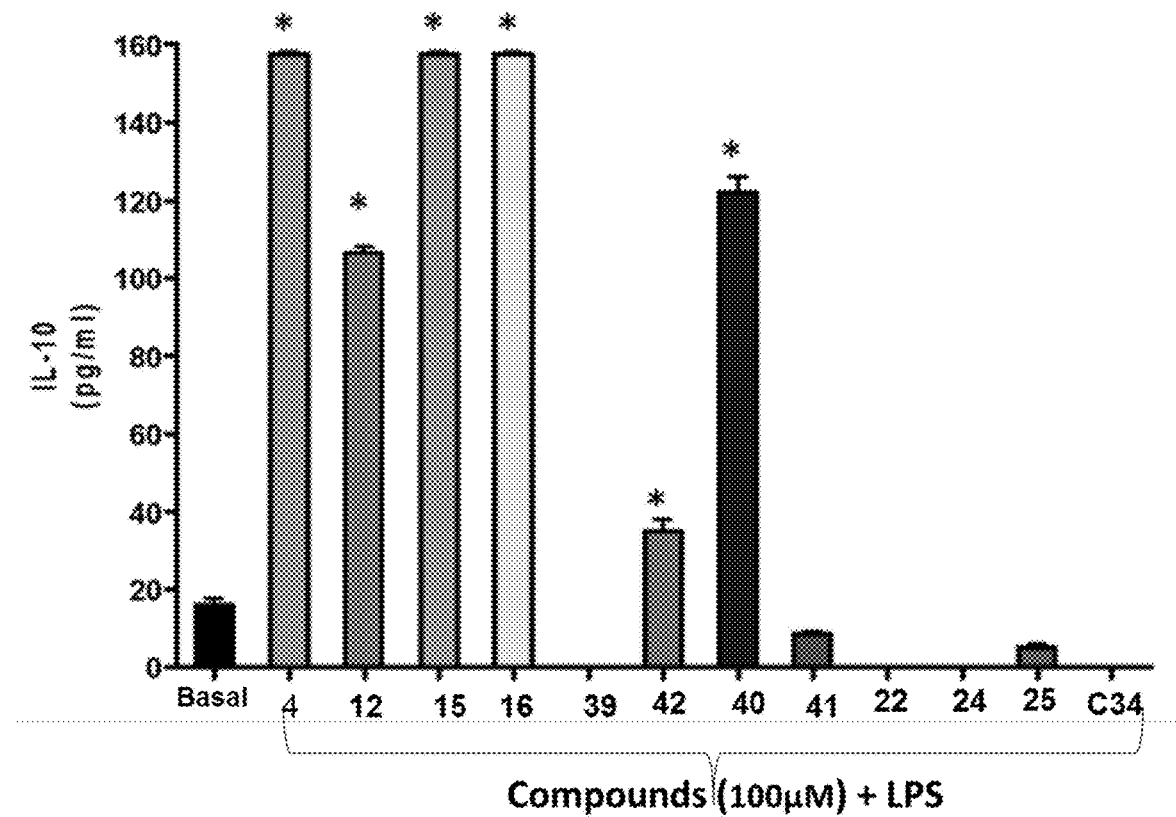
FIG. 11 demonstrates that compounds of present invention produce anti-inflammatory cytokine IL-10.

Interleukin 10 (IL-10) is a cytokine with potent anti-inflammatory properties that plays a central role in limiting host immune response to pathogens, thereby preventing damage to the host and maintaining normal tissue homeostasis. Dysregulation of IL-10 is associated with enhanced immunopathology in response to infection as well as increased risk for development of many autoimmune diseases. Here we evaluated the compounds of present invention in upregulating the IL-10 levels in PBMC using ELISA assay (FIG. 11). Briefly, 0.5 million cells were grown in RPMI with 10% FBS O/N in two 24 well plate. Next day, the media was taken out without disturbing the lower layer and different concentration of compounds (0, 1, 10, 100 µM) were added to make total amount of 0.5 ml volume with RPMI which was incubated for 48 hrs. Cells were harvested and the collected soup was analyzed using ELISA kit following manufacturer's instruction (Raybiotech).

Example 6

Chitohexaose (Compound 1) Protected Mouse from Lethal Gram Negative Sepsis Against *E. Coli*

In an in vivo mice model, chitohexaose (Compound 1) protected mouse from lethal gram negative sepsis against *E. coli*. Previously reported bacterial sepsis model [Roger etal, Proc Natl Acad Sci USA. 2009 Feb 17;106(7):2348-52] was recruited to study the efficacy of Compound 1 (FIG-1). Intraperitoneally $2 \times 10^5$ CFU of *E. coli* (ATCC-25922) was injected into BALB/c mice with and without Compound 1 (250 µg/animal). *E. coli* mediated sepsis induced mortality whereas simultaneous treatment of mice with Compound 1 protected (40%) from sepsis induced death. The above result explained that bacteria induced sepsis and mortality is inhibited and delayed for a certain period of time which may provide a window for therapy.

Example 7

Compound 4, 15 and 25 Protected Mice from CLP Induced Polymicrobial Infection Infection and Sepsis To prove the concept and demonstrate the feasibility, we have tested compound 4 in mouse model of CLP. The CLP model consists of perforation of the cecum allowing the release of fecal material into the peritoneal cavity to generate an exacerbated immune response induced by polymicrobial infection. This model fulfills the human condition that is clinically relevant. Previously reported CLP sepsis protocol (Toscano et al, Journal of Visualized Experiments: 2011, (51), 2860] was recruited to study the efficacy of compound 4. Compound 4 (10 mg/kg) was injected intravenously into C57BL/6 mice (Jackson Laboratories, 10-12 weeks, N=15) into CLP group and CLP plus saline (0.5%) and antibiotics (primaxin, 5 mg/kg) after 16, 40 h post-surgery. As a result, CLP mediated sepsis induced organ dysfunction and death whereas simultaneous treatment of mice with compound 4 protected (~93%) mice from sepsis induced death (14/15) as shown in FIG. 2. We have also demonstrated that in combination with the standard point of care anti-biotics primaxin (5 mg/kg), compound 4 protected (~93%) mice from sepsis induced death (14/15) and simultaneously delayed the clinical symptoms such as body temperature lowering, shivering, huddling, loss of appetite, decreased movement, higher heart and respiratory rate.

Figure 5:
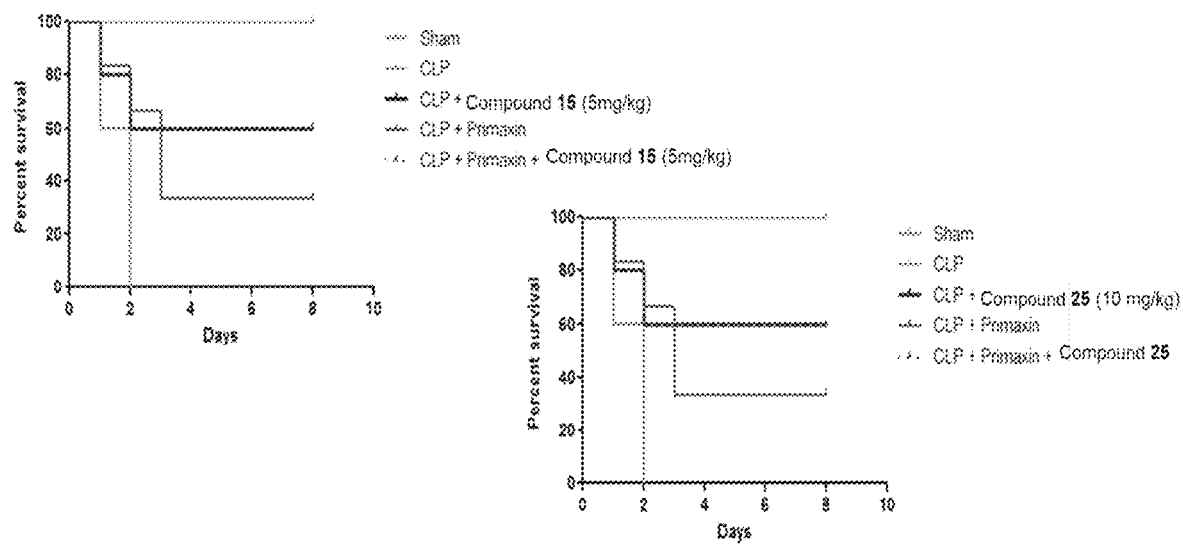
FIG. 5 is graphs showing the results of an evaluation of the compound 15 and 25 of the present invention in a cecal ligation and puncture (CLP) model and illustrates that both compounds protected mice from CLP induced polymicrobial sepsis and death.

Compound 25 (10 mg/kg) and Compound 15 (5.0 mg/kg) also protected (~60%) mice from sepsis induced death as shown in FIG. 5. We have also demonstrated that in combination with the standard point of care anti-biotics primaxin (5 mg/kg), both the compounds protected (~60%) mice from sepsis induced death and simultaneously delayed the clinical symptoms such as body temperature lowering, shivering, huddling, loss of appetite, decreased movement, higher heart and respiratory rate.

Example 8

Histopathology of Organ Tissues Post-CLP Mice

Hematoxylin Eosin (H/E) staining of different organs of Sham, CLP and compound 4 treated mice were done. Briefly, after tissues were collected they were fixed in 10% buffered neutral formalin, processed, embedded in paraffin and sectioned at 4µ for routine hematoxylin-eosin staining. CLP mice showed micro thrombi and congestion in the heart, lungs, liver, kidney and brain, increased germinal centers size in spleen, necrosis of villi in gut and loss of testicular epithelium. On treatment with compound 4, all these changes were reversed to a major extent and tissues resembled to sham group (FIG. 3).

Example 9

Biomarker Study of the Post-CLP Serum

The plasma collected from tail vein 48 h post-surgery were stored at −30° C. and were analyzed for TNF-α, IL-6, and IL-1β levels for the Sham, CLP, CLP+compound 4, CLP+primaxin, CLP+primaxin+compound 4 and control (saline injected) groups. Compound 4 alone or in combination with antibiotics primaxin decreased the level of TNF-α, IL-1β and IL-6 statistically significant (n=4, p<0.0005) in compared to CLP group of mice (FIG. 4). Briefly commercially available ELISA Kit was used to estimate the above cytokines by a sandwich ELISA method. The ELISA plates were coated with capture antibodies followed by incubation with test samples and appropriate standards. Then it was probed with biotin labeled secondary antibodies and avidin-peroxidase. Color was developed using TMB and optical density (OD) was recorded.

Example 10

Compounds of Present Invention have Broad-Spectrum Antimicrobial Activity

Figures 12, 13:
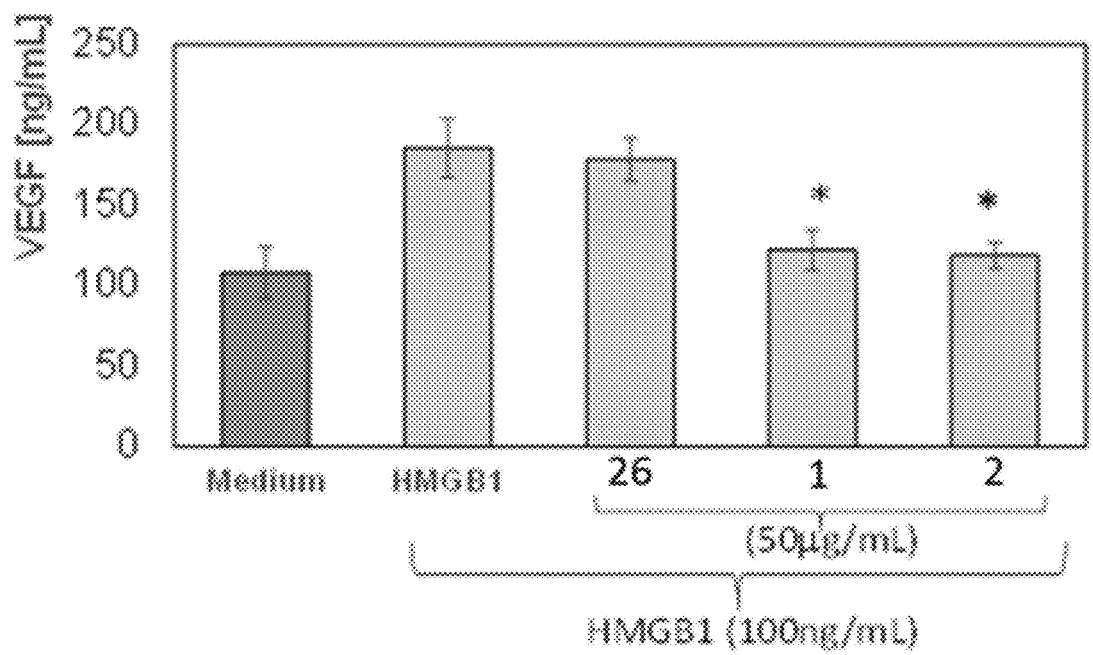
FIG. 12 demonstrates that compounds of present invention (1, and 2) decreased HMGB1 induced VEGF production in ARPE-19 cell.
FIG. 13 demonstrates that compounds of present invention have broad-spectrum antimicrobial activity.

The compounds were screened against selected gram negative (*E. Coli, P. Aeruginosa, A, Baumannii, K. Pneumonia*), gram positive (MRSA) as well as fungus (*C. Albicans*) mostly found in burn and septic wounds. Most of them showed antimicrobial activity with $MIC_{90}$ of 50-200 mg/L (FIG. 13). All prepared compounds have been evaluated in a Minimum Inhibitory Concentrations (MIC) assay with both test and control articles in accordance with guidelines of the Clinical Laboratory Standards Institute (CLSI) for broth microdilution susceptibility testing. Briefly, test and control compounds have been dissolved in DMSO, diluted to proper concentrations and added to 96-well microdilution trays. Brain Heart Infusion Broth (BHI) was used for studies with bacterial strains such as *S. aureus, E. coli, P. Aeruginosa, K pneumoniae, A. baumannii* and *Candida albicans*. Compounds were diluted serially from 200 µg/ml to 0.0625 µg/ml and plated in 96 well plates, and inoculated with approximately $1 \times 10^5$ CFU of each organism. The MIC endpoint was determined for each compound after 24 hrs as the lowest concentration of test or control compound which completely inhibits growth of the organism in microdilution.

Example 11

Compounds of Present Invention Inhibited Biofilm Formation

Based on the in vitro antimicrobial MIC data, we have selected three compounds 1, 12 and 15 for further study against MRSA. All three compounds demonstrated better activity against MRSA and MSSA strains compared to colistin (standard of care antibiotic) which was used as positive control (FIG. 14). Further we studied their biofilm inhibition and eradication activities against biofilm cells as described previously [Ceri et al, *Journal of Clinical Microbiology* 1999, 37, 1771-1776]. The minimum biofilm eradication concentrations (MBIC) of compound 15 were superior to colistin for MRSA. Thus, these compounds with activities against *S. aureus* biofilms will have significant impact on controlling recalcitrant biofilm-mediated endovascular infections [Li et al, J Infect Dis. 2016 Nov. 1;214 (9):1421-1429; Archer et al, *Virulence* 2011, 2, 445-459]. Briefly, we used Calgary Biofilm Device (CBD) technology for the biofilm susceptibilities to compounds. The CBD produces 96 equivalent biofilms for the assay of antibiotic susceptibilities by the standard 96-well technology. Susceptibility to a standard group of compounds and antibiotics was determined for National Committee for Clinical Laboratory Standards (NCCLS) as described previously.

Example 12

The Broad-Spectrum Antimicrobial Activity of the Compounds of Present Invention is Via Disruption of Cell Membrane The effects of the AVR compounds on exponentially growing MRSA and membrane integrity were evaluated.

Figure 15:
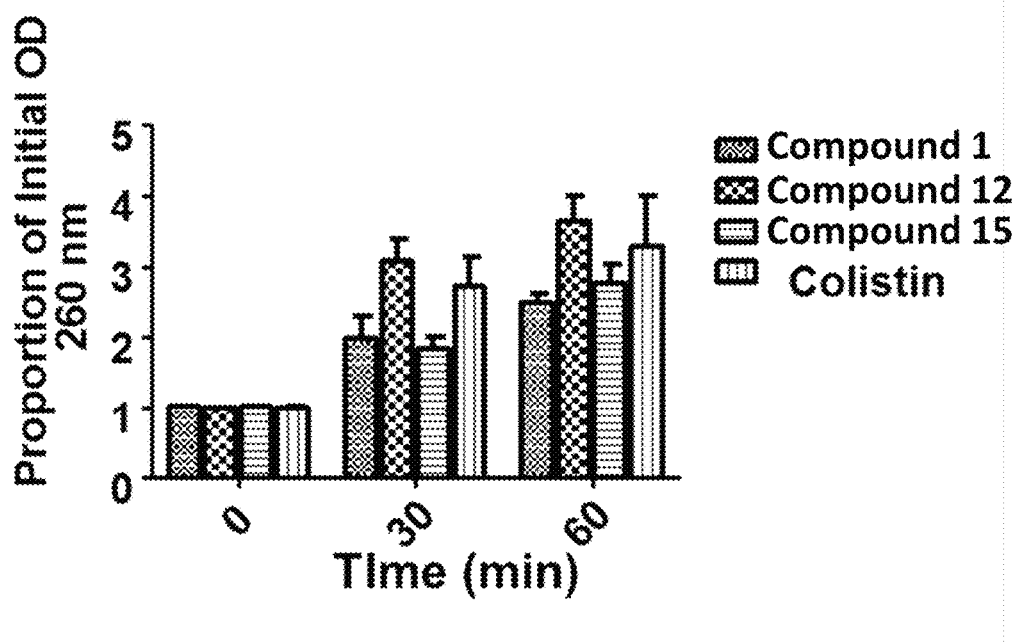
FIG. 15 demonstrates that the broad-spectrum antimicrobial activity of the compounds of present invention is via disruption of cell membrane.

MRSA re-suspended in phosphate-buffered saline was exposed to antibiotics as well as AVR compounds 1, 12 and 15 at their MIC value in brain heart infusion broth for 30 min and 1 hour before measuring the absorbance of leaked cellular material detected at an optical density of 260 nm in the culture filtrate (FIG. 15).

Example 13

Compounds of Present Invention do not Bind to the Plasma Serum Protein

Figure 16:
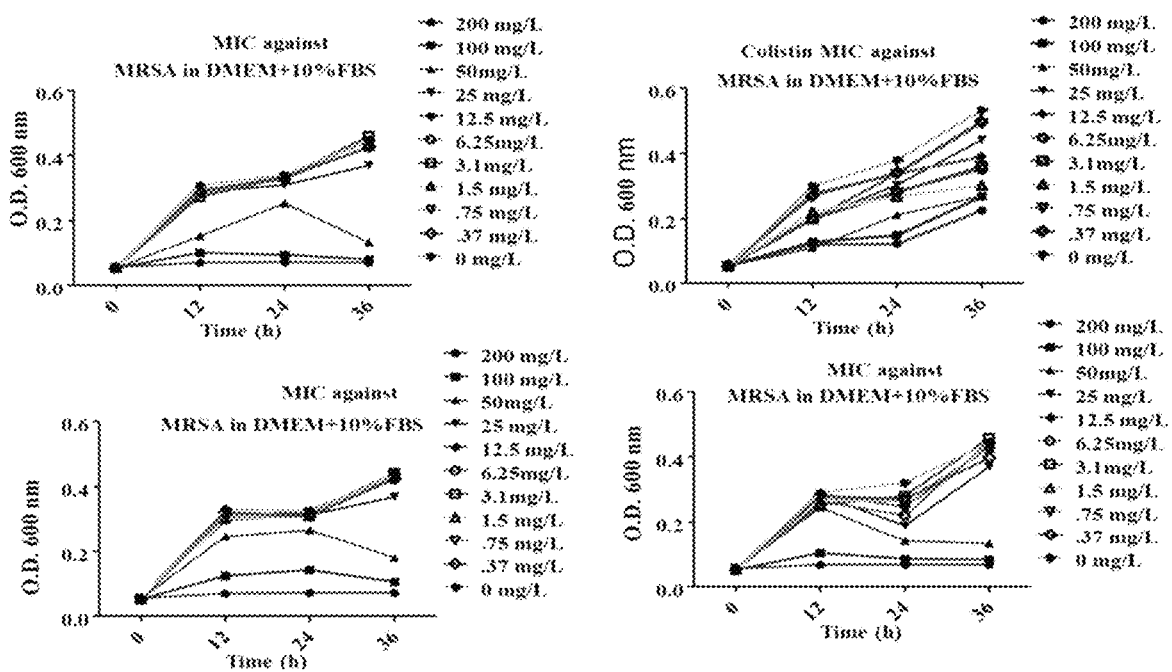
FIG. 16 demonstrates that compounds of present invention don't bind to the plasma serum protein.

One of the major difficulty in designing systemic, oral or topical drug candidate is their poor plasma/tissue bioavailability due to binding of the drug to the plasma serum protein. So, we have studied the effect of serum on compounds activities by microdilution MICs in DMEM containing 10% bovine serum (GIBCO, MA) [Hurdle et al, Journal of Antimicrobial Chemotherapy 2008, 62, 1037-1045]. The results showed (FIG. 16) that all compounds were active against MRSA and didn't bind to the serum protein suggesting them to have good bioavailability in the target tissue.

Example 14

Compounds of Present Invention are not Toxic to Fibroblast Cells

Figure 17:
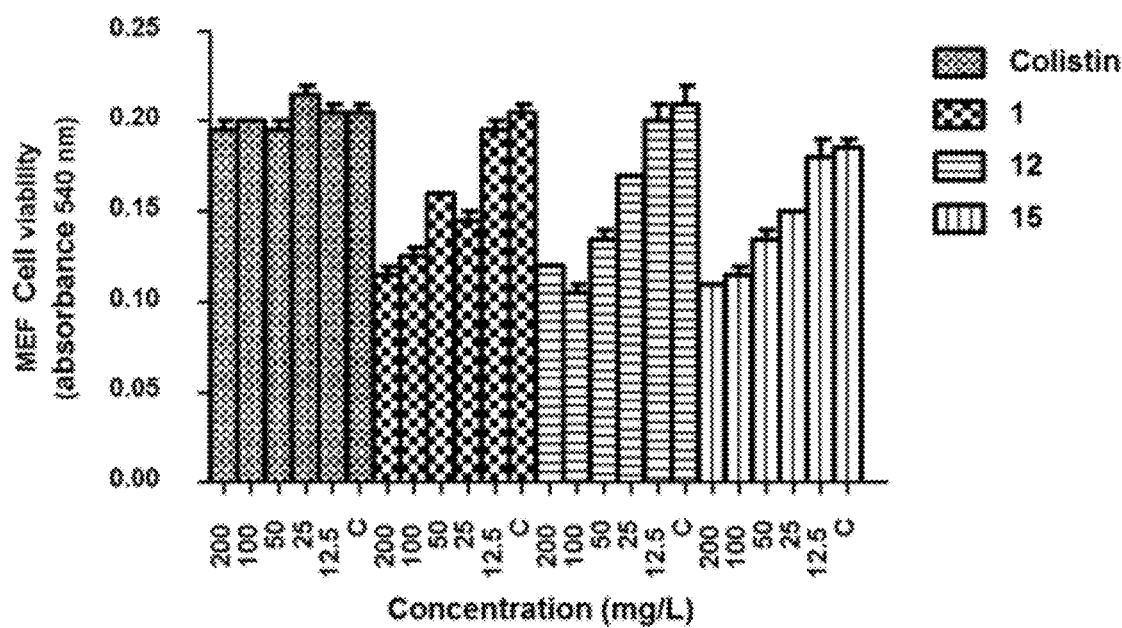
FIG. 17 demonstrates that compounds of present invention are not toxic to fibroblast cells.

Cytotoxicity and therapeutic index were also evaluated by exposing to MEF mouse fibroblast cell lines (ATCC, Manassas, Va.) to antibiotic colistin and AVR compounds for 24 h, followed by an MTT [3-(4,5-dimethyl-2-thiazolyl)-2,5-diphenyl-2H-tetrazolium bromide, Thermo Fischer, MA] assay as described previously. The cytotoxicity for all the AVR compounds in MEF mouse fibroblast cell line is shown in FIG. 17, indicating that AVR compounds selectively inhibit the growth of MRSA without compromising the growth of fibroblast cells which are critical in wound healing process.

Example 15

Compounds 1 and 2 Decreased VEGF Production in ARPE-19 Cell

Central to photoreceptor survival and function, the RPE is the major source of the angiogenic factor VEGF and therefore plays a central role in the modulation and progression of choroidal neovascularization [Spilsbury et al, The American Journal of Pathology 2000, 157, 135-144; Betts et al, ISRN Ophthalmology 2011, 2011, 184295] leading to AMD. As part of our preliminary result to evaluate if compounds 1 and 2 can inhibit the HMGB1 (an endogenous ligand for TLR4) induced VEGF production in ARPE-19 cells. FIG. 12 showed that compounds 1 and 2 (50 µg/mL) effectively reduced the HMGB1 induced VEGF production in ARPE-19 cells in a statistically significant manner (p<0.01). $2 \times 10^5$ ARPE-19 cells were seeded in 24 well plate for 24 h in full medium containing 10% serum following which they were maintained for additional 24 h with serum free medium. Cells were treated with 0 µg/mL (medium) or 100 ng/mL of HMGB1 along with or without of 50 µg/mL of test compounds for 24 h. Supernatant was collected and assayed using human VEGF ELISA kit from Peprotech according to manufacturer's instructions. RPE cells are located adjacent to choroidal capillaries and other major ocular vasculatures. Thus these finding suggests that compounds 1 and 2 may have a significant effect on the inhibition of angiogenesis (via inhibiting TLR4 and decreasing VEGF) of choroidal as well as retinal capillaries, which contribute to the development of AMD and retinopathy.

Example 16

Compound 2 Decreased the Choroidal Neovascularization ~60% as Compared to the Positive Control in a Lased Induced CNV Mouse Model for Wet AMD To demonstrate the in vivo angiostatic effects of the AVR compounds, we have tested the compounds in mouse model of laser-induced CNV (FIG. 5). Laser CNV was induced in C57BL/6 (10-12 weeks) mice using an Iridex Oculight GL 532 nm diode laser (Mountain View, Calif.) connected to the Micron IV fundus imaging system using a laser injector (Phoenix Research Laboratories, Pleasanton, Calif.). The parameters used to reproducibly obtain successful laser spots (as confirmed by a gas bubble formation indicating rupture of Bruch membrane) were: 350 mW, 75 msec, and 50 µm spot size. Four laser spots were applied; 2-3 disc diameters from the optic nerve. Mice were treated with either PBS (negative control), Compound 1, 2, and 26 or a positive control (anti-VEGF antibody) on days 2, 4 and 6 after laser (n=4-6 mice/group). Compounds 1, 2, 26 and BSS (vehicle) were administered by IP injection once daily, and was started one day before laser and continued for 10 days after laser. By the end of the experiment, mouse eyes were examined by fundus fluorescein angiography and/or optical coherence tomography (OCT) to visualize the CNV lesions. Afterwards animals were sacrificed and RPE/choroid/sclera flat mounts were prepared and stained with both FITC-conjugated isolectin B4 and anti-ICAM-2 antibody to quantitatively measure the size of CNV. We have performed two experiments to test the effects of 1, 2, 26 on laser-induced CNV. As shown in FIG. 5, 200 µg daily i.p. injection of compound 2 was able to reduce the average size of CNV lesions to about 60% of those in control mice treated with vehicle only (balanced salt buffer) and comparable to the positive control.

Example—17

Synthesis of Compound 11

To chitotriose (10 mg, 0.015 mmol) in 5 mL of methanol, a methanolic solution of 4-carboxy-TEMPO (4.5 mg, 0.026 mmol) was added. To this a methanolic solution of DCC (4.66 mg, 0.026 mmol) and cat DMAP was added and stirred at room temperature for 48 h, chilled at 2° C. for 12 h. Ether was added to precipitate white solid, filtered and dried to provide 4.0 mg of white powder. LC/MS=684 (M$^+$1); $^1$H NMR (DMSO-D$_6$, 500 MHz): d 1.15 (s, 12H), 1.35-1.55 (m, 4H), 1.97-2.05 (bs, 10H), 2.43 (m, 1H), 2.80-3.23 (m, 4H), 3.25-3.66 (m, 11H), 4.07 (s, 2H), 4.41 (s, 2H), 4.65 (s, 2H), 5.18 (d, 1H), 5.52 (bs, 2H), 8.15 (d, 1H, NH).

Synthesis of Compound 30

To a stirred suspension of D-glucosamine 29 (100 g, 0.55 mol) in EtOH (500 mL), NaOEt (30 g, 0.55 mol) was added. After 10 minutes, the mixture was treated with dimethylmaleic anhydride (0.5 eq) and stirred for 20 minute. Triethylamine (65.2 mL, 0.465 mol) was added and the reaction mixture was again treated with remaining dimethylmaleic anhydride (0.5 eq). The reaction mixture was warmed to 60° C. with stirring for 2 h, EtOH was evaporated and dried. The residue was treated with pyridine, acetic anhydride and stirred at room temp for 20 h. The reaction was monitored by TLC, the solvent was evaporated and the residue poured in to ice, extracted with chloroform (3×1 L), washed with aqueous hydrochloric acid (3%) 1L, saturated sodium bicarbonate solution (1 L), distilled water (1L), dried with anhydrous sodium sulfate. The residue was purified by silica gel chromatography using EtOAc (20-30%) in pet-ether as eluent to get compound 30 (80 g, ~37%). $^1$H NMR (400 MHz, CDCl$_3$): δ 1.91 (3H, s), 1.94 (6H, s), 2.01 (s, 3H), 2.03 (s, 3H), 2.09 (s, 3H), 3.92-3.96 (m, 1H), 4.0-4.12 (dd, 1H), 4.18-4.23 (dd, 1H), 4.30-4.33 (dd, 1H, J=4.4 Hz), 5.14 (t, 1H, J=9.2 Hz), 5.69 (t, 1H, J=9.2 Hz), 6.34 (d, 1H, J=8.8 Hz).

Synthesis of Compound 31

To a solution of 30 (100 g, 0.219 mol) in DMF, slowly added hydrazine hydrate (12 ml, 0.219 mol) at 23° C., stirred same temp for 5-6 h, and monitored by TLC. The reaction mixture was diluted with ethyl acetate (2 L) and washed with water (3×1 L), brine (1 L) and dried over Na$_2$SO$_4$ and evaporated to get compound 31 (65 g, ~71%). $^1$HNMR (400 MHz, CDCl$_3$): δ 1.85 (s, 3H), 1.90 (s, 6H), 1.98 (s, 3H), 2.05 (s, 3H), 3.79-3.84 (m, 1H), 3.95-4.06 (dd, 1H), 4.10-4.13 (dd, 1H), 4.20-4.24 (dd, 1H), 5.06 (t, 1H, J=9.6 Hz), 5.42 (d, 1H, J=8.4 Hz), 5.60 (t, 1H, J=9.6 Hz).

Synthesis of Compound 32

To a stirred solution of compound 31 (35 g, 0.084 mol) and imidazole (14.4 g, 0.211 mol) in DCM, was added TBDMSCl (15.2 g, 0.101 mol) portion wise at 23° C. and stirred at same temp for 16 h, monitored by TLC, diluted with DCM (1 L), washed with water (2×1 L), brine (500 mL), dried over Na$_2$SO$_4$ and concentrated to get crude. The residue was purified by silica gel chromatography using EtOAc (15-20%) in pet-ether as eluent to afford compound 32 (27 g, ~61%). $^1$H NMR (400 MHz, CDCl$_3$): δ 0.01 (s, 3H), 0.05 (s, 3H), 0.76 (s, 9H), 1.91 (s, 3H), 1.93 (s, 6H), 2.01 (s, 3H), 2.07 (s, 3H), 3.80-3.83 (m, 1H), 3.98-4.03 (dd, 1H), 4.10-4.14 (dd, 1H), 4.20-4.24 (dd, 1H), 5.05 (t, 1H, J=9.6 Hz), 5.36 (d, 1H, J=8.4 Hz), 5.66 (t, 1H, J=9.6 Hz).

Synthesis of Compound 33

To a stirred solution of compound 32 (27 g, 0.051 mol) in MeOH (100 mL), was added NaOMe (2.76 g, 0.052 mol) portion wise at 23° C. and stirred at same temp for 3-4 h. The reaction was monitored by TLC, MeOH was concentrated under reduced pressure and diluted with 50 mL water, pH was adjusted to 6.5-7.0, the solid was filtered and dried to get pure compound 33 (16 g, ~77%). $^1$H NMR (400 MHz, CDCl$_3$): δ 0.03 (s, 3H), 0.05 (s, 3H), 0.76 (s, 9H), 1.94 (s, 6H), 3.45-3.47 (m, 1H), 3.57-3.61 (m, 1H), 3.77-3.90 (m, 3H), 4.21 (t, 1H, J=8.0 Hz), 5.23 (d, 1H, J=8.0 Hz).

Synthesis of Compound 34

A suspension of compound 33 (30 g, 0.074 mol) and dibutyltin oxide (37.25 g, 0.149 mol) in toluene (400 mL) was heated under reflux for 12 h, tetrabutylammonium iodide (55.2 g, 0.149 mol) and benzyl bromide (25.5 g, 0.149 mol) were added and the mixture was gently refluxed for 3 h, the reaction mixture was cooled, concentrated to get crude. The residue was purified by silica gel chromatography by using 15-20% EtOAc in pet-ether to yield 34 (25 g, ~60%). $^1$H NMR (400 MHz, CDCl$_3$): δ 0.06 (s, 3H), 0.02 (s, 3H), 0.73 (s, 9H), 1.83-1.93 (bs, 6H), 3.56-3.61 (m, 1H), 3.72-3.80 (m, 2H), 3.86-3.89 (dd, 1H), 4.09-4.14 (dd, 1H), 4.53 (d, 1H, J=12 Hz), 4.56-4.63 (dd, 2H), 4.69-4.76 (dd, 2H), 5.16 (t, 1H, J=8.0 Hz), 7.15-7.24 (m, 5H), 7.33-7.37 (m, 5H).

Synthesis of Compound 35

To a mixture of compound 31 (5 g, 0.012 mol) and CCl$_3$CN (2.06 g, 0.014 mol) in dry CH$_2$Cl$_2$ was added DBU (0.37 g, 0.002 mol) and stirred at RT for 15-16 h. The reaction mixture was concentrated to get crude. The crude was purified by silica gel chromatography by using EtOAc (25-35%) in pet-ether to yield 35 (3.8 g, 55%). $^1$H NMR (400 MHz, CDCl$_3$): δ 1.91 (s, 3H), 1.93 (s, 6H), 2.01 (s, 3H), 2.07 (s, 3H), 3.93-4.01 (m, 1H), 3.98-4.03 (dd, 1H), 4.33-4.40 (m, 2H), 5.20 (t, 1H, J=9.2 Hz), 5.73 (t, 1H, J=9.2 Hz), 6.45 (d, 1H, J=9.2 Hz), 8.67 (s, 1H).

Synthesis of Compound 36

A mixture of 35 (4 g, 0.007 mol) and 34 (3.3 g, 0.0057 mol) is taken in oven dried round bottom flask containing activated molecular sieves powder)(4A°. Then the RB was back filled with argon twice and added dry DCM (10 mL), stirred at 23° C. for 2 h. Then resulting reaction mixture was cooled to −10° C. and added 0.1M solution of TfOH in DCM and further stirred for 16 h. The reaction mixture was concentrated under reduced pressure to get crude mixture which was purified by silica gel chromatography by using EtOAc (25-35%) in pet-ether to yield 36 (2 g, 30%). $^1$H NMR (400 MHz, CDCl$_3$): δ 0.005 (s, 3H), −0.11 (s, 3H), 0.71 (s, 9H), 1.76 (bs, 6H), 1.90 (s, 3H), 1.95 (bs, 6H), 1.98 (s, 3H), 3.36-3.44 (m, 3H), 3.48-3.55 (m, 3H), 3.80-3.83 (m, 2H), 3.90-3.93 (dd, 1H), 4.04-4.12 (m, 3H), 4.14-4.20 (dd, 1H), 4.42 (d, 1H, J=12.4 Hz), 4.57-4.64 (dd, 2H), 4.81 (d, 1H, J=12.4 Hz), 5.03-5.08 (m, 2H), 5.36 (d, 1H, J=8.4 Hz), 5.61 (t, 1H, J=9.2 Hz), 7.13-7.19 (m, 5H), 7.33-7.39 (m, 5H).

Synthesis of Compound 37

To a solution of compound 36 (5.5 g, 0.0056 mol) in dry THF (50 mL) was added AcOH (0.36 mL, 0.0063 mol) and cooled to −5° C. Then added 1 M TBAF (6.3 mL, 0.0063 mol) soln in THF at −5° C. stirred at room temperature for 16 h. After completion of the reaction, reaction mixture was quenched with sat NaCl solution, extracted with DCM and concentrated under reduced pressure to obtain crude compound 37 (3 g, crude) which was used further reaction without purification. $^1$H NMR (400 MHz, CDCl$_3$): δ 1.76 (s, 6H), 1.89 (s, 3H), 1.95 (bs, 6H), 1.98 (s, 3H), 3.38-3.55 (m, 3H), 3.62-3.66 (m, 1H), 3.76-3.80 (m, 1H), 3.90-3.94 (m, 1H), 4.06-4.22 (m, 6H), 4.14-4.20 (dd, 1H), 4.40 (d, 1H, J=12.8 Hz), 4.57-4.64 (dd, 2H), 4.85 (d, 1H, J=12.8 Hz), 5.01-5.07 (m, 2H), 5.33 (d, 1H, J=8.4 Hz), 5.55-5.63 (t, 1H, J=9.2 Hz), 7.11-7.20 (m, 5H), 7.29-7.42 (m, 5H).

Synthesis of Compound 38

To a mixture of compound 37 (4 g, 0.0045 mol) and CCl$_3$CN (0.54 mL, 0.0054 mol) in dry CH$_2$Cl$_2$ was added DBU (0.13 mL, 0.0009 mol) stirred at RT for 15-16 h. The reaction mixture was concentrated to get crude. The crude was purified by silica gel chromatography by using EtOAc (25-35%) in pet-ether to yield 38 (1 g, 20%).

Synthesis of Compounds 39-42

A mixture of 38 (1 g, 0.89 mmol) and R—OH (0.7 eq) is taken in oven dried round bottom flask containing activated molecular sieves powder (4 A° then RB was back filled with argon twice and added dry DCM (20 mL), stirred at rt for 2 h. Then resulting reaction mixture was cooled to −10° C. and added 0.1M solution of TfOH (1.3 mL, 0.13 mmol) in DCM and further stirred for 16 h. The reaction mixture was concentrated under reduced pressure to get crude mixture. The crude was purified by silica gel chromatography by using EtOAc (25-35%) in pet-ether to yield compounds 39-42 (~40-45%).

Compound-39: $^1$H NMR (400 MHz, CDCl$_3$): δ 1.76 (s, 6H), 1.89 (s, 3H), 1.95 (bs, 6H), 1.98 (s, 3H), 3.49-3.51 (m, 2H), 3.64-3.71 (m, 2H), 3.94-3.96 (m, 1H), 4.15-4.19 (m, 6H), 4.40 (m, 1H), 4.56-4.65 (m, 2H), 4.86-4.91 (m, 1H), 5.06-5.09 (m, 1H), 5.33 (d, 1H, J=8.4 Hz), 5.55-5.63 (t, 1H, J=9.2 Hz), 6.91 (d, 2H, J=8.4 Hz), 7.12-7.21 (m, 5H), 7.29-7.42 (m, 5H), 8.06 (d, 2H, J=8.4 Hz). LC/MS: M$^+$=982.

Compound-40: $^1$H NMR (400 MHz, CDCl$_3$): δ 1.21-1.48 (m, 10H), 1.76 (bs, 6H), 1.89 (s, 3H), 1.95-1.96 (s, 9H), 1.98 (s, 3H), 3.36-3.38 (m, 1H), 3.43-3.46 (m, 3H), 3.59 (d, 1H, J=8.4 Hz), 3.89-3.92 (m, 2H), 4.04-4.08 (m, 4H), 4.41 (d, 1H, J=10.0 Hz), 4.60 (s, 2H), 4.84 (d, 1H, J=10.0 Hz), 4.93 (d, 1H, J=6.4 Hz), 5.04 (t, 1H, J=7.2 Hz), 5.35 (d, 1H, J=6.4 Hz), 5.57-5.61 (t, 1H, J=7.2 Hz), 7.13-7.19 (m, 5H), 7.28-7.40 (m, 5H), LC/MS: M$^+$-2=943.

Compound-41: $^1$H NMR (400 MHz, CDCl$_3$): δ 1.21-1.35 (m, 8H), 1.45-1.62 (bs, 8H), 1.76 (bs, 6H), 1.90 (s, 3H), 1.95-2.22 (m, 12H), 3.43-3.46 (m, 4H), 3.60-3.71 (m, 1H), 3.94 (d, 1H), 4.04-4.12 (m, 4H), 4.20 (m, 1H), 4.55-4.59 (m, 1H), 4.62-4.70 (m, 2H), 4.84 (d, 1H, J=10.0 Hz), 4.93 (d, 1H, J=6.4 Hz), 5.30 (t, 1H, J=7.2 Hz), 5.35 (m, 1H), 5.61 (t, 1H, J=7.2 Hz), 7.13-7.19 (m, 5H), 7.28-7.40 (m, 5H), LC/MS: M$^+$-2=1015.

Compound-42: $^1$H NMR (400 MHz, CDCl$_3$): δ 1.76 (s, 6H), 1.90 (s, 3H), 1.95 (s, 3H), 1.98 (s, 6H), 2.01 (s, 3H), 3.43-3.49 (m, 3H), 3.62-3.64 (m, 1H), 3.72 (s, 3H), 3.91-3.94 (m, 1H), 4.07-4.21 (m, 5H), 4.42 (d, 1H, J=12.4 Hz), 4.59 (s, 2H), 4.85 (d, 1H, J=12.4 Hz), 5.05 (t, 1H, J=10.8 Hz), 5.34-5.37 (m, 2H), 5.60 (t, 1H, J=10.8 Hz), 6.69 (d, 2H, J=9.2 Hz), 6.77 (d, 2H, J=9.2 Hz), 7.11-7.21 (m, 5H), 7.29-7.42 (m, 5H). LC/MS: M$^+$=986.

Synthesis of Compound 15

Compound 15 was synthesized from compound 39 (0.5 g) by removal of NDMM group using hydrazine hydrate in HCl followed by treatment with Ac$_2$O to introduce NHAc group. Finally removal of —OAc groups by NaOCH$_3$/MeOH at room temperature as described previously [Mohamed R. E et al, Carbohydrate research, 2001, 331, 129-142] afforded compound 15 (22 mg white solid). $^1$H NMR (400 MHz, CDCl$_3$): δ 1.98 (s, 6H), 3.43-3.49 (m, 3H), 3.62-3.64 (m, 1H), 3.72 (s, 3H), 3.91-3.94 (m, 1H), 4.23-4.42 (m, 3H), 4.62 (m, 4H), 5.90 (d, 1H, J=10.8 Hz), 6.42 (d, 1H, J=10.8 Hz), 6.91 (d, 2H, J=8.4 Hz), 7.12-7.21 (m, 5H), 7.29-7.42 (m, 5H), 8.06 (d, 2H, J=8.4 Hz). LC/MS: M$^+$=710.

Synthesis of Compound-43

To a stirred suspension of D-glucosamine 29 (200 g, 0.93 mol) in pyridine was added acetic anhydride (720 mL, 7.4 mol). The reaction mixture was warmed to 60° C. with stirring for 12 h (monitored by TLC), the reaction mixture was concentrated under reduced pressure. The residue poured in to ice, extracted with chloroform (3×1 L), washed with aqueous hydrochloric acid (3%) 1 L, saturated sodium bicarbonate solution (1 L), distilled water (1 L), dried by anhydrous sodium sulfate. The crude mixture 43 was preceded to next step without further purification.

Synthesis of Compound 44

To a solution of 43 (30 g, 77.09 mmol) in THF, slowly added Methyl amine in MeOH (2M, 77 mL, 154.1 mmol)) at RT and stirred same temp for 12 h, monitored by TLC. The reaction mixture was diluted with ethyl acetate (2 L) and washed with water (3×1 L), brine (1 L) and dried over Na$_2$SO$_4$ and evaporated. To get compound 44 (20 g).

Synthesis of Compound-45

A mixture of 44 (20 g, 0.057 mol), CCl$_3$CN (11 mL, 0.114 mol), and DBU (2.5 mL, 0.0014 mol) in dry CH$_2$Cl$_2$ was stirred at RT for 15-16 h. The reaction mixture was concentrated to get crude. The crude was purified by silica gel chromatography by using EtOAc (25-35%) in pet-ether to yield compound 45 (5 g). $^1$H NMR (400 MHz, CDCl$_3$): δ 1.91 (s, 3H), 1.93 (s, 3H), 2.01 (s, 3H), 2.07 (s, 3H), 3.93-4.01 (m, 1H), 3.98-4.03 (dd, 1H), 4.33-4.40 (m, 2H), 5.20 (t, 1H, J=9.2 Hz), 5.73 (t, 1H, J=9.2 Hz), 6.45 (d, 1H, J=9.2 Hz), 8.67 (s, 1H).

Synthesis of Compound-24

To a stirred suspension of 45 (2 g, 5.14 mmol) and 4-OH-TEMPOL (0.7 g, 4.11 mmol) in DCM with molecular sieves powder stirred for 2 h at RT, Triflic acid (0.11 g, 0.77 mmol) was added and stirred for 4 h at RT. The RM was distilled and purified by column chromatography eluted with 5% MeOH in DCM to provide compound 24 (300 mg). $^1$H NMR (400 MHz, CDCl$_3$): δ 1.14 (s, 12H), 1.41-1.66 (m, 4H), 1.91 (s, 3H), 1.93 (s, 3H), 2.01 (s, 3H), 2.07 (s, 3H), 4.15-4.36 (m, 4H), 5.30 (d, 1H, J=9.2 Hz), 5.73 (t, 1H, J=9.2 Hz), 6.45 (d, 1H, J=9.2 Hz). TLC system: 10% MeOH in DCM, R$_f$: 0.3.

Synthesis of Compound 25

To a stirred solution of compound 24 (0.3 g, 0.79 mmol) in MeOH, was added NaOMe (0.04 g, 0.63 mmol) at RT and stirred at same temp for 3-4 h. The reaction mixture was monitored by TLC, MeOH was concentrated, neutralized with 1 M Dioxane in HCl. The RM was concentrated and purified by column chromatography with 7% MeOH in DCM as eluent to get compound 25 (50 mg). $^1$H NMR (400 MHz, CDCl$_3$): δ 1.14 (s, 12H), 1.41-1.66 (m, 4H), 1.93 (s, 3H), 4.15-4.36 (m, 4H), 5.30 (d, 1H, J=9.2 Hz), 5.73 (t, 1H, J=9.2 Hz), 6.45 (d, 1H, J=9.2 Hz). LC/MS: M$^+$=374. TLC system: 10% MeOH in DCM, R$_f$: 0.2.

Example—18

Topical/Intravitral Formulation

The table below represents exemplary ranges for a topical or intravitrael ophthalmic composition according to the present invention:

| Ingredients | w/v % |
| --- | --- |
| Compound 2 | 0.1 to 1.5 |
| Mannitol | 2.0 |
| Sodium acetate | 0.5 |
| Acetic acid | 0.02 |
| PEG 8000 | 2.0 |
| Polysorbate 80 | 1.0 |
| HPMC | 0.5 |
| Sodium hydroxide/ Hydrochloric acid | For adjusting pH 6.5-7.4 |
| Water | Q.S. to 100 |

Example—19

Injectable Formulation

The table below represents exemplary ranges for an intravenous (IV) composition according to the present invention: The compound of the invention is dissolved in most of the water (35° 40° C.) and the pH adjusted to between 4.0 and 7.0 with the hydrochloric acid or the sodium hydroxide as appropriate. The batch is then made up to volume with water and filtered through a sterile micropore filter into a sterile 10 mL, amber glass vial (type 1) and sealed with sterile closures and over seals.

| Ingredients | Amount |
| --- | --- |
| Compound 15, 25 | 5-10 mg/kg |
| Hydrochloric Acid Solution 0.1M or | 4.0 to 7.0 (pH) |
| Sodium Hydroxide Solution 0.1M q.s. to pH | 4.0 to 7.0 (pH) |
| Sterile water q.s. to | 10 mL |

Example—20

The tables below represents exemplary ranges for topical gel, lotion and spray compositions according to the present invention:

Gel Formulation:

The table below represents exemplary ranges for gel composition according to the present invention: Disperse the Carbomer 934 uniformely in about 40% of total amount of water. Add the ammonia solution gradually into the dispersion with agitation to form a clear gel. In a separate container dissolve the methyl paraben in prolylene glycol and then disperse 10.0 g of compound 15 in this solution to make a homogenous suspension. Gradually add the suspension into the gel with agitation, a uniform white opaque gel will be obtained.

| Ingredient | Amount |
| --- | --- |
| Compound 15 | 10.0 g |
| Carbomer 934 | 3.0 g |
| Propylene Glycol | 40 mL |
| Strong ammonia solution | 4.0 mL |
| Methyl paraben | 3.0 g |
| Purified water, USP q. s to | 1000 g |

Cream or Lotion Formulation:

The table below represents exemplary ranges for cream or lotion composition according to the present invention: dissolve the methyl paraben in about 80% of total amount of prolylene glycol. Add the poloxyl 2 cetyl ether into this solution with agitation. In a separate processing container mix the 20% of the propylene glycol, part of the purified water and 10.0 g of compound 15 to form a uniform suspension. Gradually add the suspension into the first processing container with moderate stirring until a homogenous, soft, white cream is obtained Pass the cream through a colloid mill and bring the mass of the batch to the targeted quantity.

| Ingredient | Amount |
| --- | --- |
| Compound 15 | 10.0 g |
| Poloxyl 2 cetyl ether | 50.0 g |
| Propylene Glycol | 50 mL |
| Methyl paraben | 3.0 g |
| Purified water, USP q. s to | 1000 g |

Non-Aerosol Spray Formulation:

The table below represents exemplary ranges for non-aerosol spray composition according to the present invention: 5.00 g of polyoxyl 10 oleyl ether is dissolved in 188.75 g of castor oil with gentle stirring. 25.0 g of compound 15 and 25.0 g of zinc oxide were suspended to the slurry with moderate stirring followed by 1.25 g of fumed silica gel. The slurry is mixed under high shear stress until uniform and smooth and packaged in a spray bottle.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

| Ingredient | Amount |
| --- | --- |
| Compound 15 | 25.0 g |
| Zinc oxide | 25.0 g |
| Castor oil | 188.75 g |
| Polyoxy 10 oleyl ether | 5 g |
| Fumed silica | 1.25 |

In so far as the description above and the accompanying drawings disclose any additional subject matter, the inventions are not dedicated to the public and the right to file one or more applications to claim such additional inventions is reserved.

REFERENCES

Leon, Carlos G.; Tory, Rita; Jia, Jessica; Sivak, Olena; Wasan, Kishor M. a. Pharmaceutical Research (2008), 25(8), 1751-1761.

Savva Athina; Roger Thierry From Frontiers in immunology (2013), 4387, Language: English, Database: MEDLINE Cho, Y.; Wang, J. J.; Chew, E. Y.; Ferris, F. L.; Mitchell, P.; Chan, C.-C.; Tuo, J., Toll-like Receptor Polymorphisms and Age-Related Macular Degeneration: Replication in Three Case-Control Samples. Investigative Ophthalmology & Visual Science 2009, 50, (12), 5614-5618.

Higgins, G. T.; Wang, J. H.; Dockery, P.; Cleary, P. E.; Redmond, H. P., Induction of angiogenic cytokine expression in cultured RPE by ingestion of oxidized photoreceptor outer segments. Invest Ophthalmol Vis Sci. 2003, 44(4): 1775-82

Kaarniranta, K.; Salminen, A., Age-related macular degeneration: activation of innate immunity system via pattern recognition receptors. J Mol Med (Berl). 2009, 87(2):117-23.

Elner, S. G.; Petty, H. R.; Elner, V. M.; Yoshida, A.; Bian, Z.-M.; Yang, D.; Kindezelskii, A. L., TLR4 mediates human retinal pigment epithelial endotoxin binding and cytokine expression. Transactions of the American Ophthalmological Society 2005, 103, 126-137.

Yi, H.; Patel, A. K.; Sodhi, C. P.; Hackam, D. J.; Hackam, A. S., Novel Role for the Innate Immune Receptor Toll-Like Receptor 4 (TLR4) in the Regulation of the Wnt Signaling Pathway and Photoreceptor Apoptosis. PLoS One 2012, 7, (5), e36560.

He, C.; Sun, Y.; Ren, X.; Lin, Q.; Hu, X.; Huang, X.; Su, S.-B.; Liu, Y.; Liu, X., Angiogenesis mediated by toll-like receptor 4 in ischemic neural tissue. Arterioscler Thromb Vasc Biol. 2013, 33(2):330-8.

Huang, J.-D.; Amaral, J.; Lee, J. W.; Rodriguez, I. R., 7-Ketocholesterol-Induced Inflammation Signals Mostly through the TLR4 Receptor Both In Vitro and In Vivo. PLoS One 2014, 9, (7), e100985.

CN 102475714.

CN 101732338.

US 20020022601.

Hadwiger, Lee A.; Klosterman, S.; Chang, M.-M.; Friel, P.; Hosick, H. L., From Advances in Chitin Science (1997), 2, 102-109.

EP 183556.

Xu, Ke; Chen, Jun-quan Zhongguo Laonianxue Zazhi (2012), 32(24), 5478-5480.

Wang, Jianyun; Chen, Yuanwei; Ding, Yulong; Shi, Guoqi; Wan, Changxiu, Applied Surface Science (2008), 255(2), 260-262.

Xiong, Chuannan; Wu, Haige; Wei, Peng; Pan, Ma; Tuo, Yaqin; Kusakabe, Isao; Du, Yuguang, Carbohydrate Research (2009), 344(15), 1975-1983.

CN102085212.

Opal, S. M.; Laterre, P.; Francois, B.; et al., Effect of eritoran, an antagonist of md2-tlr4, on mortality in patients with severe sepsis: The access randomized trial. JAMA 2013, 309, 1154-1162.

Wong, W. L.; Su, X.; Li, X.; Cheung, C. M. G.; Klein, R.; Cheng, C.-Y.; Wong, T. Y., Global prevalence of age-related macular degeneration and disease burden projection for 2020 and 2040: a systematic review and meta-analysis. The Lancet Global Health 2014, 2, e106-e116.

Harrell, S. N.; Brandon, D. H., Retinopathy of Prematurity: The Disease Process, Classifications, Screening, Treatment, and Outcomes. Neonatal Network 2007, 26, 371-378.

Cho, Y.; Wang, J. J.; Chew, E. Y.; Ferris, F. L.; Mitchell, P.; Chan, C.-C.; Tuo, J., Toll-like Receptor Polymorphisms and Age-Related Macular Degeneration: Replication in Three Case-Control Samples. Investigative Ophthalmology & Visual Science 2009, 50, 5614-5618.

He, C.; Sun Y Fau-Ren, X.; Ren X Fau-Lin, Q.; Lin Q Fau-Hu, X.; Hu X Fau-Huang, X.; Huang X Fau-Su, S.-B.; Su Sb Fau-Liu, Y.; Liu Y Fau-Liu, X.; Liu, X., Angiogenesis mediated by toll-like receptor 4 in ischemic neural tissue.

Xia, W.; Liu, P.; Zhang, J.; Chen, J., Biological activities of chitosan and chitooligosaccharides. Food Hydrocolloids 2011, 25, 170-179.

Mosser, D. M., The many faces of macrophage activation. Journal of Leukocyte Biology 2003, 73, 209-212.

Panda, S. K.; Kumar, S.; Tupperwar, N. C.; Vaidya, T.; George, A.; Rath, S.; Bal, V.; Ravindran, B., Chitohexaose Activates Macrophages by Alternate Pathway through TLR4 and Blocks Endotoxemia. PLoS Pathog 2012, 8, e1002717.

Roger, T.; Froidevaux C Fau-Le Roy, D.; Le Roy D Fau-Reymond, M. K.; Reymond Mk Fau-Chanson, A.-L.; Chanson Al Fau-Mauri, D.; Mauri D Fau-Burns, K.; Burns K Fau-Riederer, B. M.; Riederer Bm Fau-Akira, S.; Akira S Fau-Calandra, T.; Calandra, T., Protection from lethal gram-negative bacterial sepsis by targeting Toll-like receptor 4.

Ceri, H.; Olson, M. E.; Stremick, C.; Read, R. R.; Morck, D.; Buret, A., The Calgary Biofilm Device: New Technology for Rapid Determination of Antibiotic Susceptibilities of Bacterial Biofilms. Journal of Clinical Microbiology 1999, 37, 1771-1776.

Li, L.; Cheung, A.; Bayer, A. S.; Chen, L.; Abdelhady, W.; Kreiswirth, B. N.; Yeaman, M. R.; Xiong, Y. Q., The Global Regulon sarA Regulates beta-lactam Antibiotic Resistance In Methicillin-resistant Staphylococcus aureus (MRSA) In Vitro and In Endovascular Infections. The Journal of infectious diseases 2016.

Archer, N. K.; Mazaitis, M. J.; Costerton, J. W.; Leid, J. G.; Powers, M.

E.; Shirtliff, M. E., Staphylococcus aureus biofilms: Properties, regulation and roles in human disease. Virulence 2011, 2, 445-459.

Hurdle, J. G.; Yendapally, R.; Sun, D.; Lee, R. E., Evaluation of Analogs of Reutericyclin as Prospective Candidates for Treatment of Staphylococcal Skin Infections. Antimicrobial Agents and Chemotherapy 2009, 53, 4028-4031.

Hurdle, J. G.; Lee, R. B.; Budha, N. R.; Carson, E. I.; Qi, J.; Scherman, M. S.; Cho, S. H.; McNeil, M. R.; Lenaerts, A. J.; Franzblau, S. G.; Meibohm, B.; Lee, R. E., A microbiological assessment of novel nitrofuranylamides as anti-tuberculosis agents. Journal of Antimicrobial Chemotherapy 2008, 62, 1037-1045.

Spilsbury, K.; Garrett, K. L.; Shen, W.-Y.; Constable, I. J.; Rakoczy, P. E., Overexpression of Vascular Endothelial Growth Factor (VEGF) in the Retinal Pigment Epithelium Leads to the Development of Choroidal Neovascularization. The American Journal of Pathology 2000, 157, 135-144.

Betts, B. S.; Parvathaneni, K.; Yendluri, B. B.; Grigsby, J.; Tsin, A. T. C.,

Ginsenoside-Rbl Induces ARPE-19 Proliferation and Reduces VEGF Release. ISRN Ophthalmology 2011, 2011, 184295.

What is claimed is:

1. A pharmaceutical composition comprising a compound according to Formula (I), or a pharmaceutically acceptable salt thereof:

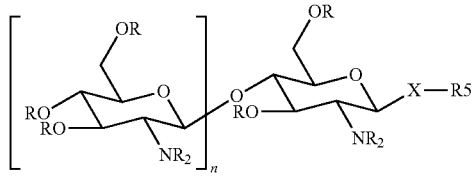

Formula I where:
R=H, C(O)R₁, alkyl, benzyl, substituted benzyl
R₁=alkyl, piperidine nitroxyl
R₂=H, C(O)R¹ or aceloxy alkyl carbamate of the following formula:
  C(O)OCHR₃OC(O)OR₄, or piperidine nitroxyl, wherein
R₃=H, CH₃, C₂H₅, isopropyl
R₄=a substituted alkyl group
X=O and is linked to the anomeric carbon via R stereochemistry (beta anomer) at a pH of 6.5-7.4
R₅=piperidine nitroxyl, piperidine N-hydroxylamine,

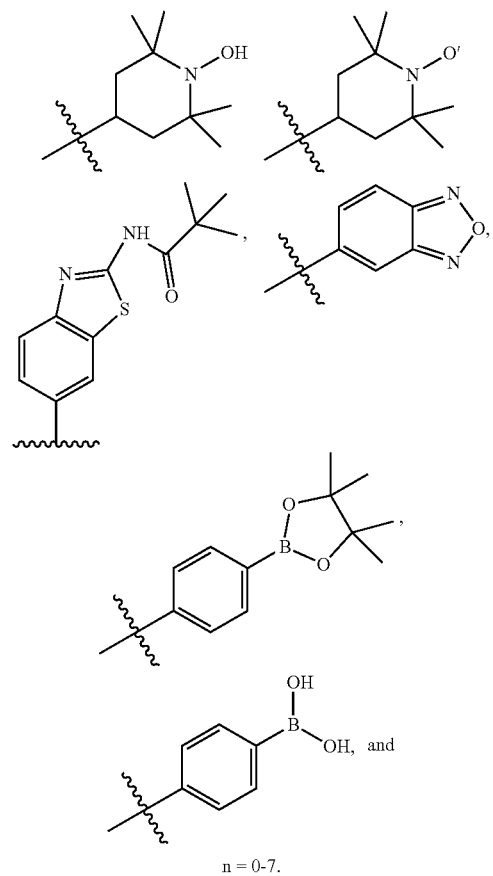

n = 0-7.

n=0-7.

2. The pharmaceutical composition of claim 1, wherein the composition is formulated as a sterile, injectable aqueous or oleaginous suspension.

3. The pharmaceutical composition of claim 1, wherein the composition is formulated as a sterile topical gel, ointment or aqueous spray.

4. The pharmaceutical composition of claim 1, further comprising an anti-inflammatory agent or an anti-microbial agent.

5. The pharmaceutical composition of claim 1, further comprising one or more vehicles selected from alcohols and ketones emollients, hydrocarbon oils and waxes, lanolin and lanolin derivatives, silicone oils, monoglyceride, diglyceride, and triglyceride esters, fatty alcohols, alkyl and alkenyl esters of fatty acids, alkyl and alkenyl diesters of dicarboxylic acids, polyhydric alcohols and their ether and ester derivatives, wax esters beeswax derivatives, polypropylene glycol, polyethylene glycol, diisopropyl sebacate, isopropyl myristate, methyl laurate, silicone, glycerine and mixtures thereof.

6. The pharmaceutical composition of claim 1, wherein R=H or C(O)CH₃.

7. The pharmaceutical composition of claim 1, wherein R₂=C(O)CH₃.

8. The pharmaceutical composition of claim 1, wherein the compound is selected from the group consisting of:

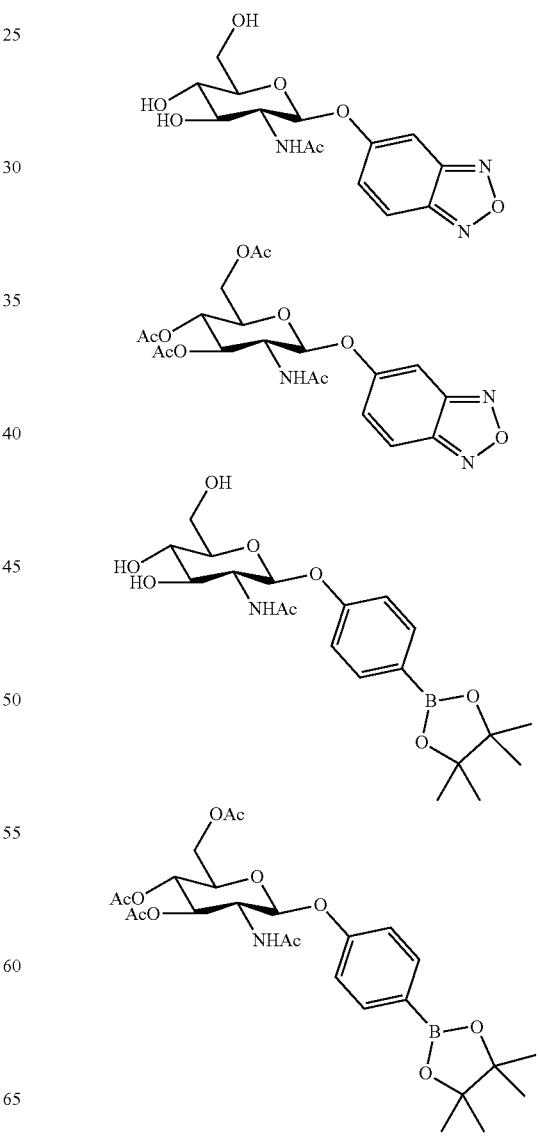

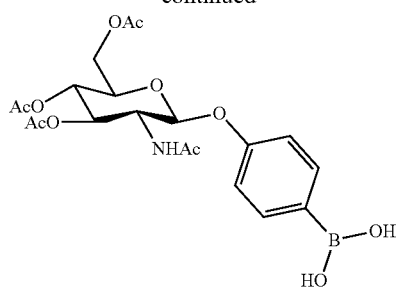
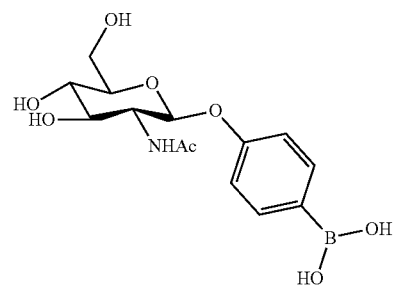
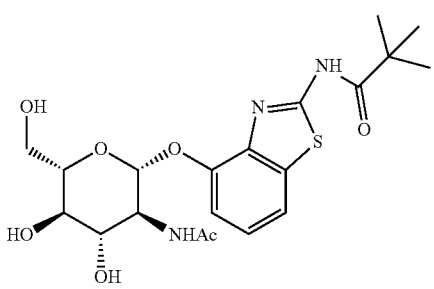
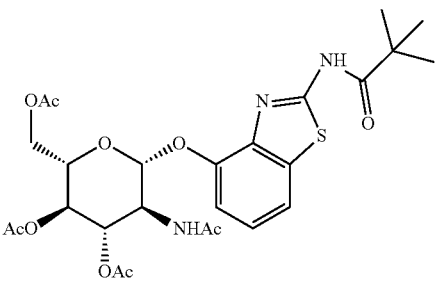
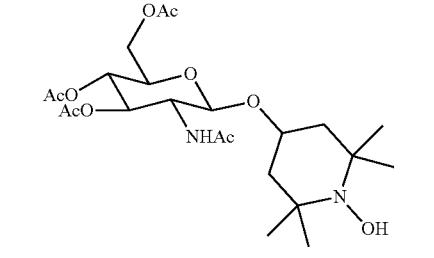
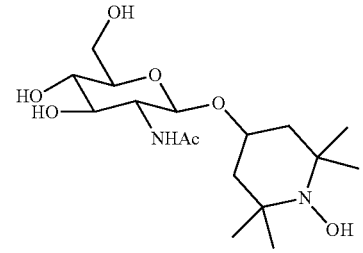
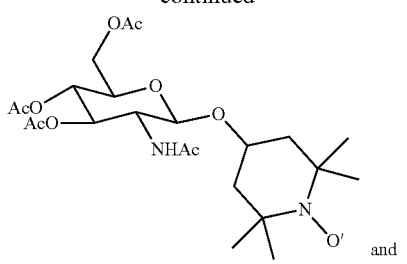
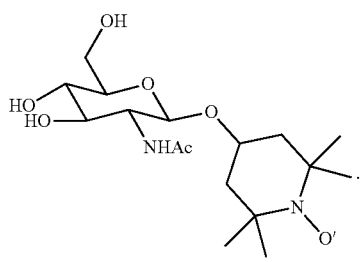
9. A pharmaceutical composition comprising one or more compounds or a pharmaceutically acceptable salt thereof selected from:
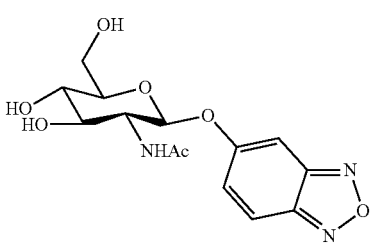
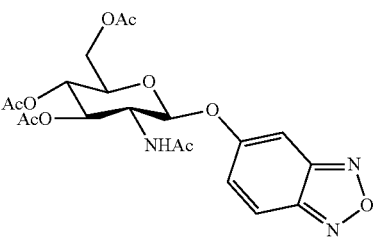
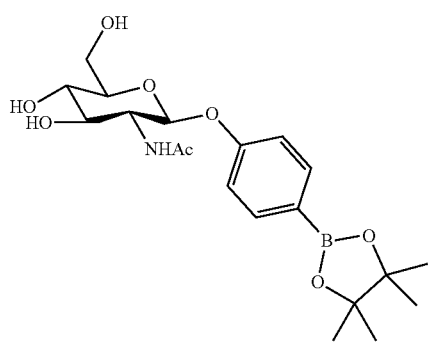

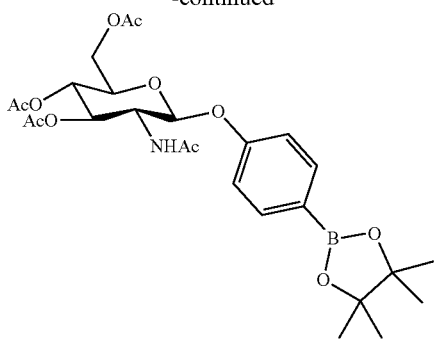
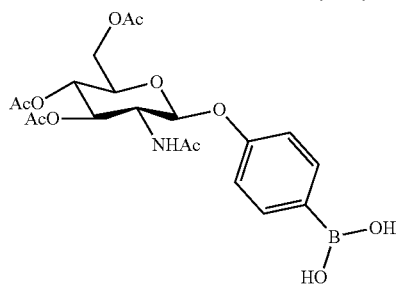
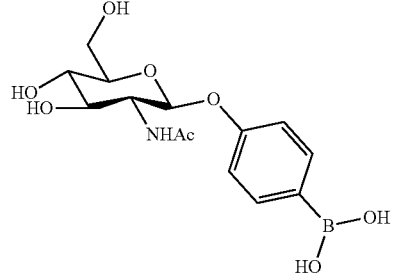
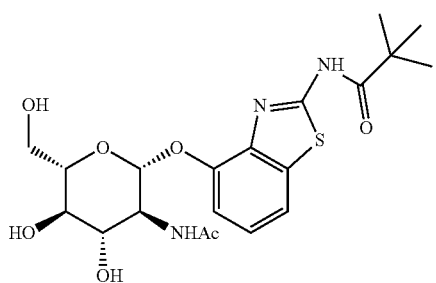
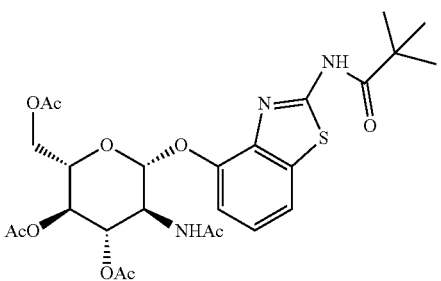
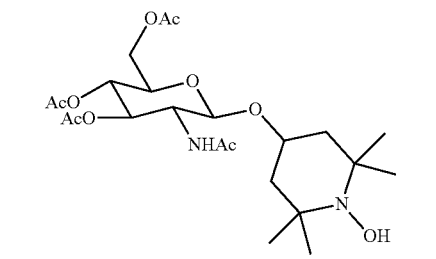

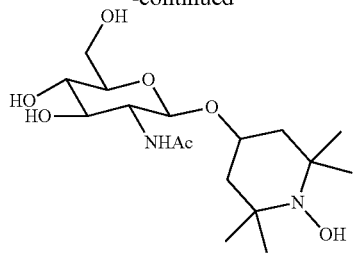
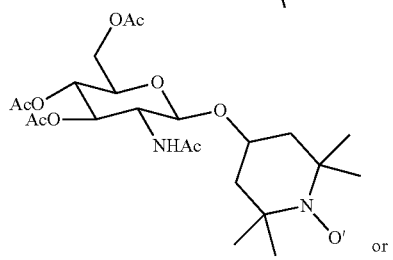
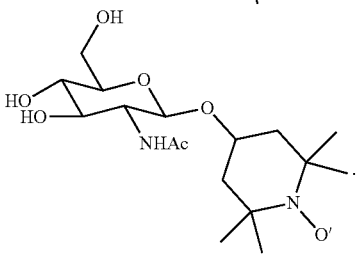

10. A pharmaceutical composition comprising a compound according to Formula (I), or a pharmaceutically acceptable salt thereof, at a pH of 6.5-7.4:

Formula I

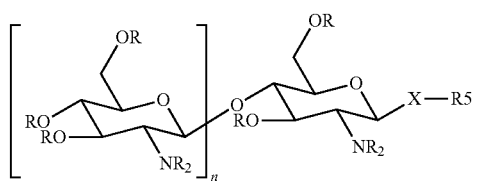

where:
R═H, C(O)R$_1$, alkyl, benzyl, substituted benzyl
R$_1$═alkyl, piperidine nitroxyl
R$_2$═H, C(O)R$^1$ or aceloxy alkyl carbamate of the following formula:
 C(O)OCHR$_3$OC(O)OR$_4$, or piperidine nitroxyl, wherein
R$_3$═H, CH$_3$, C$_2$H$_5$, isopropyl
R$_4$═a substituted alkyl group
X═O and is linked to the anomeric carbon via R stereochemistry (beta anomer)
R$_5$═heterocycloalkyl, piperidine nitroxyl, piperidine N-hydroxylamine,

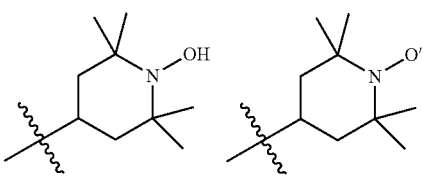

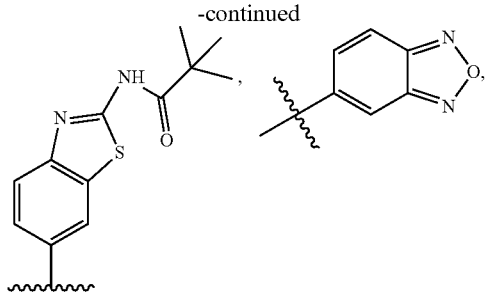
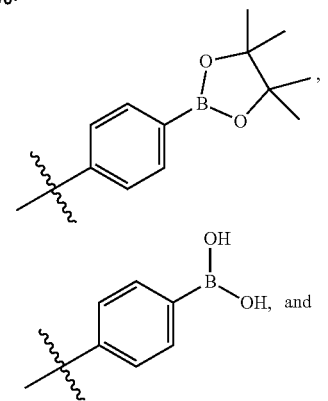
n = 0-7.
* * * * *